US009804093B2

(12) United States Patent
Schultz et al.

(10) Patent No.: US 9,804,093 B2
(45) Date of Patent: Oct. 31, 2017

(54) ULTRASENSITIVE SERS FLOW DETECTOR

(71) Applicant: University of Notre Dame du Lac, Notre Dame, IN (US)

(72) Inventors: Zachary Schultz, Granger, IN (US); Oluwatosin Dada, Everett, WA (US); Pierre Negri, South Bend, IN (US); Kevin Jacobs, Mishawaka, IN (US)

(73) Assignee: University of Notre Dame du Lac, South Bend, IN (US)

( * ) Notice: Subject to any disclaimer, the term of this patent is extended or adjusted under 35 U.S.C. 154(b) by 14 days.

(21) Appl. No.: 14/722,062

(22) Filed: May 26, 2015

(65) Prior Publication Data

US 2015/0338348 A1    Nov. 26, 2015

Related U.S. Application Data

(60) Provisional application No. 62/002,495, filed on May 23, 2014.

(51) Int. Cl.
*G01N 21/65* (2006.01)
*G01N 15/14* (2006.01)
(Continued)

(52) U.S. Cl.
CPC ....... *G01N 21/658* (2013.01); *G01N 15/1404* (2013.01); *G01N 15/1429* (2013.01);
(Continued)

(58) Field of Classification Search
CPC ......... G01N 21/658; G01N 2015/1409; G01N 2015/1411; G01N 2015/1413
See application file for complete search history.

(56) References Cited

U.S. PATENT DOCUMENTS 4,440,013 A * 4/1984 Adams ............... G01N 30/74
250/343
5,439,578 A * 8/1995 Dovichi ........... G01N 27/44721
204/603
(Continued)

OTHER PUBLICATIONS

Doering, W. E., Piotti, M. E., Natan, M. J. and Freeman, R. G. (2007), SERS as a Foundation for Nanoscale, Optically Detected Biological Labels. Adv. Mater., 19: 3100-3108. doi:10.1002/adma. 200701984.*
(Continued)

*Primary Examiner* — Michael P Lapage
(74) *Attorney, Agent, or Firm* — Haukaas Fortius PLLC; Michael H. Haukaas

(57) ABSTRACT

The invention provides an apparatus and methods for label-free, chemical specific detection in flow for high throughput characterization of analytes in applications such as flow injection analysis, electrophoresis, and chromatography. A surface-enhanced Raman scattering (SERS) flow detector capable of ultrasensitive optical detection on the millisecond time scale has been developed. The device employs hydrodynamic focusing to improve SERS detection in a flow channel where a sheath flow confines analyte molecules eluted from a capillary over a planar SERS-active substrate. Increased analyte interactions with the SERS substrate significantly improve detection sensitivity. Raman experiments at different sheath flow rates showed increased sensitivity compared with the modeling predictions, indicating increased adsorption. At low analyte concentrations, rapid analyte desorption is observed, enabling repeated and high-throughput SERS detection. The flow detector offers substantial advantages over conventional SERS-based assays such as minimal sample volumes and high detection efficiency.

20 Claims, 15 Drawing Sheets
(12 of 15 Drawing Sheet(s) Filed in Color)

(51) Int. Cl.
*G01N 21/05* (2006.01)
*G01N 15/00* (2006.01)
*G01N 15/10* (2006.01)

(52) U.S. Cl.
CPC ......... *G01N 15/1434* (2013.01); *G01N 21/05* (2013.01); *G01N 2015/0053* (2013.01); *G01N 2015/1006* (2013.01); *G01N 2015/1413* (2013.01); *G01N 2021/058* (2013.01)

(56) References Cited

U.S. PATENT DOCUMENTS

| | | | |
|---|---|---|---|
| 6,149,868 | A | 11/2000 | Natan et al. |
| 6,280,960 | B1* | 8/2001 | Carr ............... G01N 15/1463 356/244 |
| 6,861,263 | B2 | 3/2005 | Natan |
| 7,226,794 | B2 | 6/2007 | Roitman et al. |
| 7,311,476 | B2* | 12/2007 | Gilbert ............... B65G 51/08 406/195 |
| 7,333,197 | B2* | 2/2008 | Fritz ............... G01N 15/147 356/213 |
| 7,432,113 | B2 | 10/2008 | Koo et al. |
| 7,442,339 | B2* | 10/2008 | Sundararajan ....... C12Q 1/6827 356/301 |
| 7,839,508 | B2* | 11/2010 | Nishikawa ............ G01N 21/05 356/445 |
| 8,563,325 | B1* | 10/2013 | Bartsch ............ B01L 3/502776 422/502 |
| 8,865,459 | B2* | 10/2014 | Narahara ........... G01N 21/6428 435/287.9 |
| 2001/0006416 | A1 | 7/2001 | Johnson |
| 2007/0229823 | A1* | 10/2007 | Sung ................ G01N 15/1463 356/336 |
| 2010/0032584 | A1* | 2/2010 | Dayong ................ G01N 15/14 250/459.1 |

OTHER PUBLICATIONS

Negri, Pierre et al., "Online SERS Detection and Characterization of Eight Biologically-Active Peptides Separated by Capillary Zone Electrophoresis," Analyst, 2015, 140, 1516-1522.
Asiala, Steven M. et al., "Charaterization of Hotspots in a Highly Enhancing SERS Substrate," Analyst, 2011, 136, 4472-4479.
Leopold, Nicolae et al., "On-Column Silver Substrate Synthesis and Surface-Enhanced Raman Detection in Capillary Electrophoresis," Analytical and Bioanalytical Chemistry, 2010, 396, 2341-2348.
Negri, Pierre et al., "Online SERS Detection of the 20 Proteinogenic L-amino Acids Separated by Capillary Zone Electrophoresis," Analyst, 2014, 139, 5989-5998.
Negri, Pierre et al., "Ultrasensitive Surface-Enhanced Raman Scattering Flow Detector Using Hydrodynamic Focusing," Analytical Chemistry, 2013, 85, 10159-10166.
Negri, Pierre et al., "Ultrasensitive Online SERS Detection of Structural Isomers Separated by Capillary Zone Electrophoresis," Chemical Communications, 2014, 50, 2707-2710.
Watson, Dakota, A et al., "A Flow Cytometer for the Measurement of Raman Spectra," Cytometry Part A, 2008, 73A, 119-128.

* cited by examiner

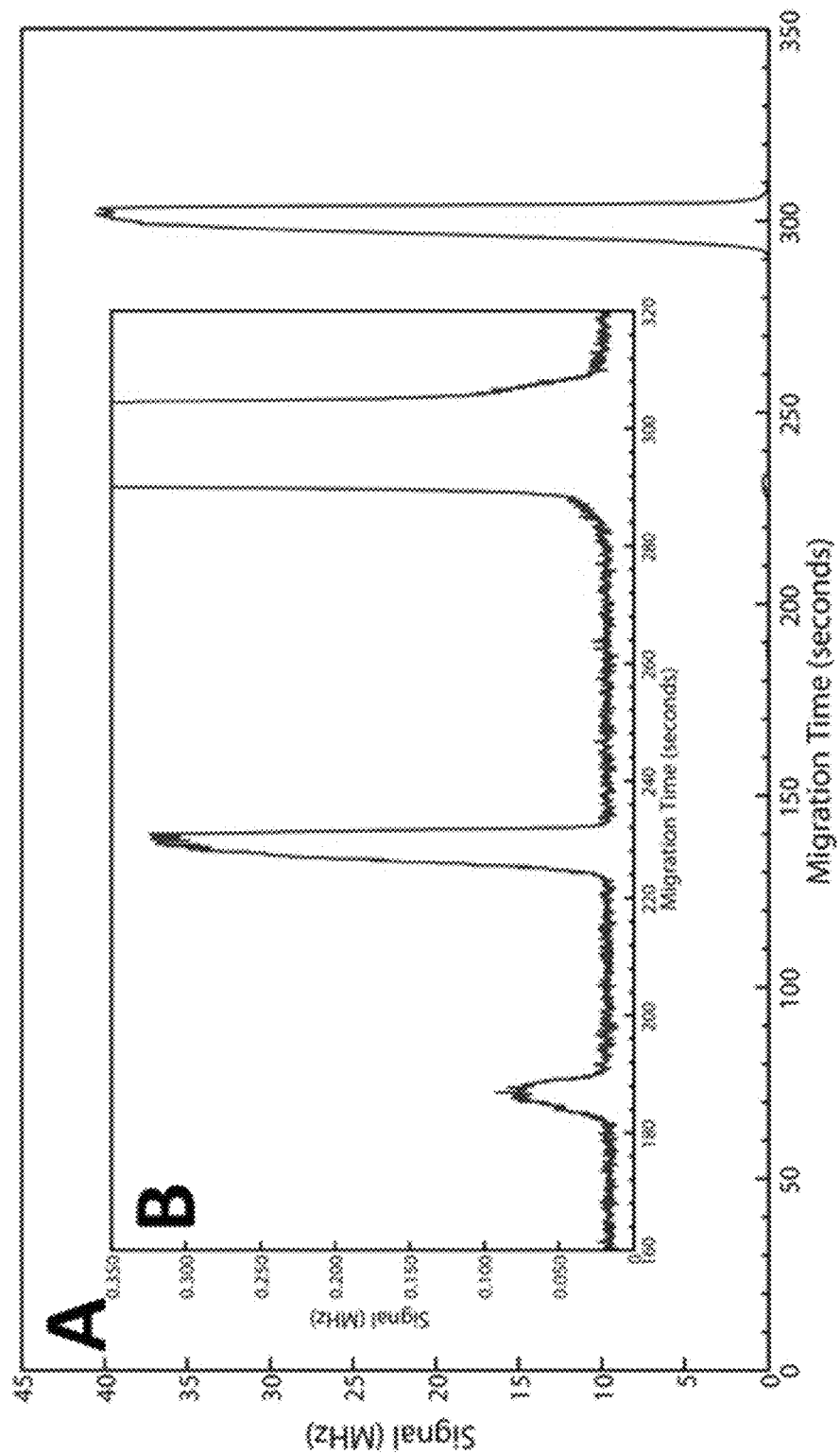
Fig. 13A-B

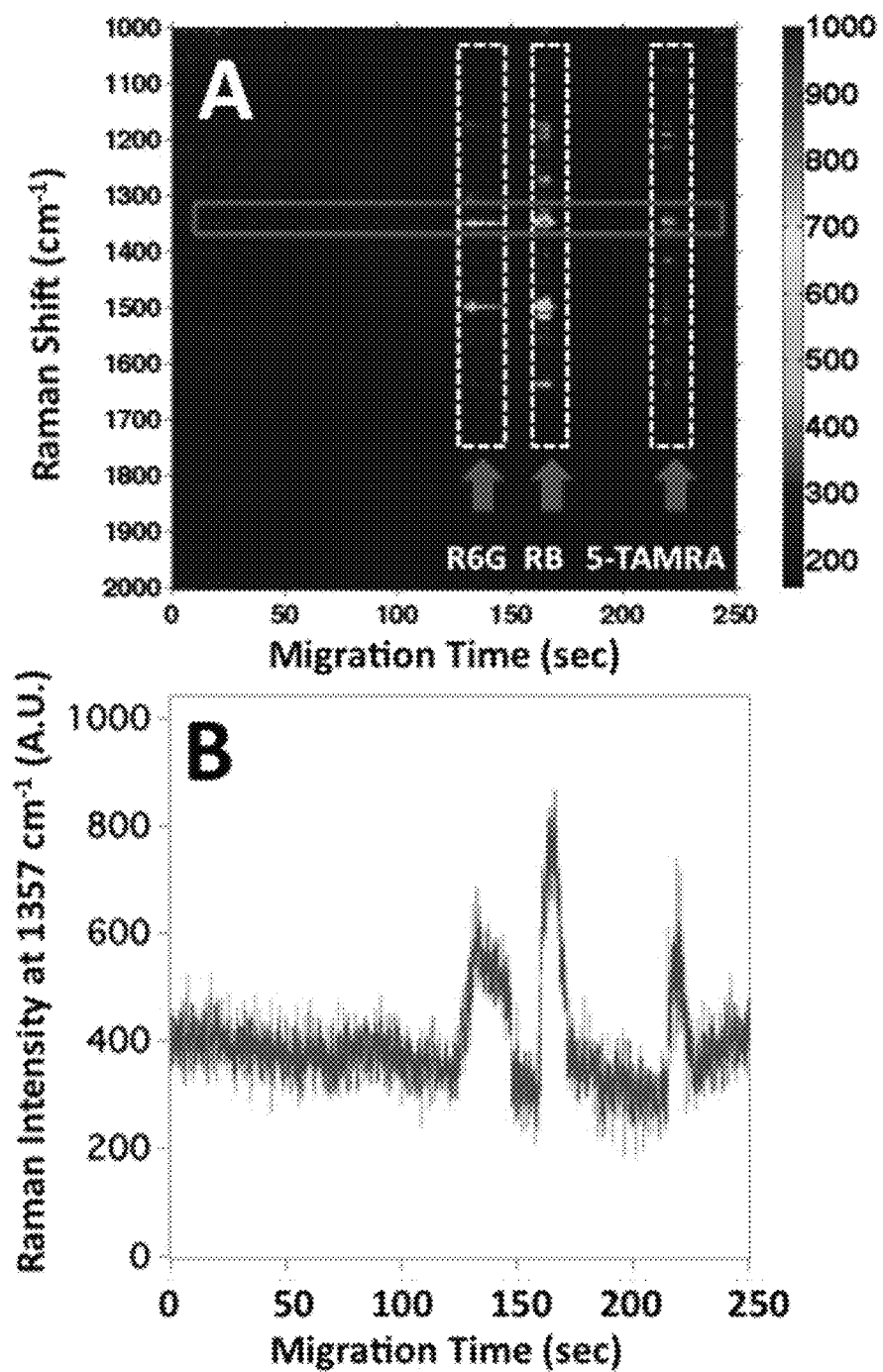
Fig. 14A-B

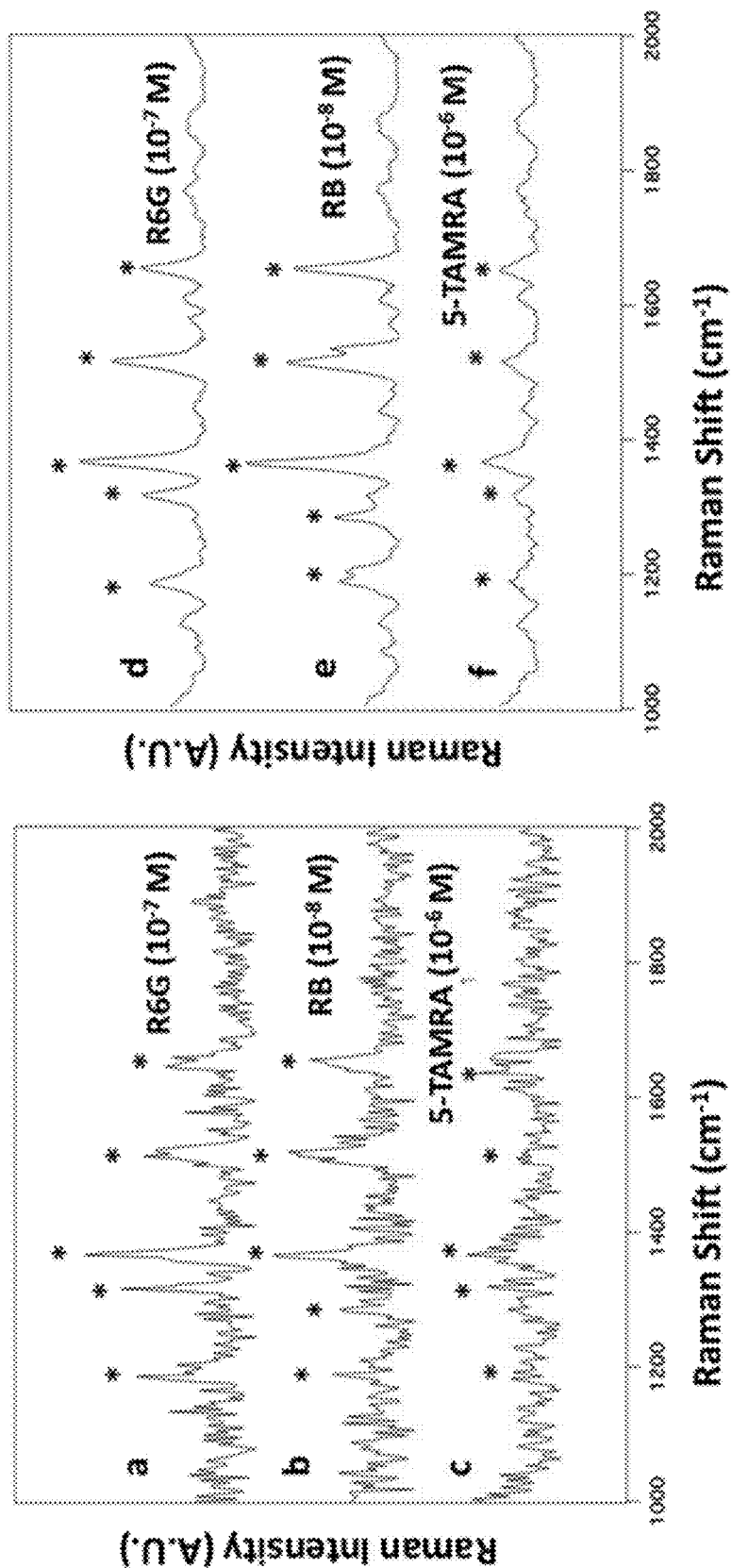
Fig. 15A-F

ULTRASENSITIVE SERS FLOW DETECTOR

RELATED APPLICATIONS

This application claims priority under 35 U.S.C. §119(e) to U.S. Provisional Patent Application No. 62/002,495, filed May 23, 2014, which is incorporated herein by reference.

GOVERNMENT SUPPORT

This invention was made with government support under Grant No. R21 GM107893 awarded by the National Institutes of Health. The government has certain rights in the invention.

BACKGROUND OF THE INVENTION

Increased understanding of surface-enhanced Raman scattering (SERS) has expanded the utility of Raman spectroscopy for a variety of applications requiring a high degree of chemical specificity. In recent years, SERS has shown tremendous potential as a powerful and ultrasensitive detection technique at the trace and even the single molecule level. One of the benefits of SERS detection is the ability to probe the structural properties of compounds in various physical environments. More particularly, the chemical specificity and insensitivity to water render SERS an ideal candidate for highly sensitive detection of analytes in aqueous environment.

High sensitivity SERS detection in flow has remained challenging. SERS originates from molecules located in close proximity to metallic nanostructures that are capable of generating a localized surface plasmon resonance (LSPR). As a result, one of the inherent requirements for SERS signal generation is that molecules must be located near the enhancing surface. This distance dependence intrinsic to SERS varies based on the type of nanostructures used for the SERS substrate. For individual nanoparticles the enhancement extends a few nanometers whereas an exponential decay of the evanescent field with a length scale of ~10 nm is observed on extended surfaces. Traditionally, depositing a solution onto a metallic nanostructure and allowing it to evaporate adsorbs molecules to the surface. In solution, however, the ability of molecules to diffuse away from the nanostructures results in limited sensitivity. It follows that the number of molecules present in the enhanced region in dilute solution is often below the limit of detection. These effects typically require micromolar or greater solution concentrations.

Nanostructure-analyte interactions in the SERS detection volume are key to improving signal sensitivity. A common approach used to promote this interaction involves mixing of the sample analyte and the colloids, either directly in a microfluidic channel or off-line prior to being introduced in the fluidic system. These techniques can achieve high sensitivity and are known to reduce problems associated with variations in sample mixing, localized heating, and photodissociation. However, the major drawbacks of using metal colloids for SERS-based assays are their lack of chemical affinity for the target analyte in solution and problems associated with non-specific adsorption that complicate detection. The random aggregation of nanoparticles is also known to affect the reproducibility of the acquired SERS spectrum. Under these conditions, SERS measurements are recorded using extended acquisition times greater or equal to one second to improve limits of detection, but limiting throughput.

Two dimensional planar substrates avoid many complications associated with nanoparticles. However, the limit of detection of 2-D substrates in solution is still controlled by transport, which can hinder analyte interaction with the SERS-active surface. Over the years, methods have been developed to increase substrate-analyte interactions. Chemical modifications have been shown to increase affinity of the analyte molecules for the SERS substrate. Such techniques concentrate nanoparticle-analyte conjugates in the detection volume to improve detection, but are limited to analytes with high affinity for the functionalized surface. Other techniques actively concentrate nanoparticle-analyte conjugates into the detection volume using electrokinetic or magnetic forces. Although these techniques improve sensitivity and the functionality of the SERS assays, the incorporation of active elements or additional fabrication steps add cost and complexity to the final device. Despite the recent advances in performance and sensitivity, these inherent drawbacks limit the successful translation of SERS from the research lab to practical applications.

Accordingly, devices and methods are needed that enable the confinement of a sample fluid near a detection surface to promote interaction between sample molecules and a SERS substrate, thereby increasing the performance and sensitivity of these analytical techniques.

SUMMARY

The invention provides an apparatus for performing surface-enhanced Raman scattering (SERS) comprising: a Raman microscope, a flow cell, an apparatus for supplying a sheath flow fluid to the flow cell, a pressure source to pump fluid through a capillary, a capillary leading from the pressure source to the flow cell, and a detector for detecting light scattered by an analyte in solution. The pressure source can be configured to transport an analyte in solution through the capillary to the flow cell, wherein the flow cell comprises: an inlet port and an outlet port for a sheath flow fluid, a planar noble metal SERS-active substrate, a capillary that connects the pressure source to the SERS-active substrate of the flow cell, wherein the end of the capillary terminates at an analyte analysis zone accessible to a laser, a flow channel extending from the end of the capillary to the analyte analysis zone for analysis of an analyte by a laser, and which concurrently define a flow path between the inlet port and the outlet port, and a flow cell cover through which a laser can be directed, which flow cell cover seals the flow cell to prevent fluid from escaping the flow cell except through the outlet port. The terminal end of the capillary can be directed toward the surface of the SERS-active substrate and the flow cell can be configured to perform hydrodynamic focusing on an analyte in solution.

In various embodiments, the invention provides an apparatus for performing surface-enhanced Raman scattering (SERS) comprising: a Raman microscope, a flow cell, an apparatus for supplying a sheath flow fluid to the flow cell, optionally a waste reservoir, a pressure source to pump fluid through a capillary; a capillary leading from the pressure source to the flow cell, and a detector for detecting light scattered by the analyte in solution. The apparatus for supplying a sheath flow fluid can be, for example, a syringe pump. The pressure source can be an inert gas supply connected to an injection block or a syringe pump. Alternatively, when the apparatus is configured to perform with applications such as capillary electrophoresis, the sample can be electrokinetically driven through the capillary.

The pressure source can be configured to transport an analyte in solution through the capillary to the flow cell, wherein the flow cell comprises: a base having an inlet port and an outlet port for a sheath flow fluid, a noble metal SERS-active substrate on the base having two holes defining the sheath flow path over the SERS-active substrate, which holes substantially match the dimensions of the inlet port and the outlet port, the capillary that connects the pressure source to the SERS-active substrate of the flow cell, wherein the end of the capillary terminates at an analyte analysis zone accessible to a laser, a gasket covering the capillary, wherein gasket has an opening over the end of the capillary, which opening defines a channel of the analyte analysis zone for analysis by a laser, and which opening defines the flow channel between the inlet port and the outlet port, and a flow cell cover through which a laser can be directed, which flow cell cover seals the flow cell to prevent fluid from escaping the flow cell except through the outlet port. The terminal end of the capillary is directed toward the surface of the SERS-active substrate so that the flow cell can be configured to perform hydrodynamic focusing on an analyte in solution.

In one embodiment, the SERS-active substrate comprises a thin film of silver metal or gold metal. The thin film can be substantially planar with a rough surface. For example, the surface nanostructure is heterogeneous, which enhances Raman scattering, and has various nanostructures including pillars of about 50 nm in diameter and of about 50 to about 150 nm in height.

In some embodiments, the capillary leading to the flow cell is a fused silica capillary.

In various embodiments, the capillary has an outer diameter of about 40 μm to about 300 μm, about 50 μm to about 150 μm, or about 125 μm to about 175 μm. In certain embodiments, the capillary has an inner diameter of about 4 μm to about 100 μm, about 10 μm to about 50 μm, about 20 μm to about 30 μm, or about 25 μm.

In some embodiments, the Raman microscope includes a single longitudinal mode laser or a diode laser. The single longitudinal mode laser can use a wavelength between about 632 nm and about 670 nm. In other embodiments, the Raman microscope includes a 660 nm diode laser or similar light source.

In one embodiment, the sample capillary is connected to a direct output of a chemical separation for repeated analysis. The chemical separation can include, for example, flow injection, electrophoresis, and chromatography applications such as liquid chromatography, HPLC, capillary electrophoresis or other solution-based separations.

The invention further provides a method of detecting or characterizing an analyte in solution using the surface-enhanced Raman scattering (SERS) apparatus described here, the method comprising:

contacting an analyte solution and a SERS-active substrate using hydrodynamic focusing to co-locate the analyte on the SERS-active substrate;

wherein the hydrodynamic focusing comprises passing a sheath fluid over the analyte in solution, wherein the ratio of the sheath flow rate to the capillary flow rate is at least 2:1, thereby increasing the adsorption and/or concentration of analytes in the detection area of the SERS-active substrate;

conducting laser excitation of the analyte on the SERS-active substrate; and detecting light scattered by the analyte in solution.

The hydrodynamic focusing on the analyte solution can confine the analyte molecules at the SERS substrate, thereby increasing the frequency of interactions between the analytes and nanostructures and increasing performance of the SERS detection. In some embodiments, the ratio of the sheath flow rate to the capillary flow rate is at least 10:1. In various embodiments, the ratio of the sheath flow rate to the capillary flow rate is about 2:1 to about 100:1. For example, the ratio of the sheath flow rate to the capillary flow rate can be about 2:1, about 5:1, about 10:1, about 12:1, about 20:1, about 25:1, about 30:1, about 36:1, about 40:1, about 45:1, about 50:1, about 70:1, about 72:1, about 80:1, about 100:1, or a range of ratios from one to any other of the aforementioned ratios. The ratio of the sheath flow rate to the capillary flow rate can also be at least about any one of the aforementioned ratios.

In one embodiment, the ratio of the sheath flow rate to the capillary flow rate is about 12:1 to about 50:1. In another embodiment, the ratio of the sheath flow rate to the capillary flow rate is about 25:1 to about 45:1.

In various embodiments, the sheath flow rate is about 50 μL/min to about 360 μL/min. In further embodiments, the sheath flow rate is about 150 μL/min to about 200 μL/min.

In some embodiments, the range of particle size detection of the flow detector is about 3000 nm to about 50 nm. In certain embodiments, the lower detection limit of the flow detector for solutions is about 100 picomolar.

In various embodiments, the signal of the Raman spectra collected is enhanced by about $10^6$ to about $10^8$ compared to a corresponding spontaneous Raman analysis that does not employ hydrodynamic focusing and SERS. In certain embodiments, the signal of the Raman spectra collected is enhanced by about $10^3$ to $10^4$ compared to a corresponding SERS analysis that does not employ hydrodynamic focusing.

In additional embodiments, the SERS-active substrate comprises a thin film of silver metal and the surface of the substrate resists fouling and lacks a memory effect of the analyte. The absence of memory effect or lack of memory effect occurs when an analyte signal is detected and returns to baseline after the analyte passes through the detection area. The analytes can be free of labels, including fluorescent labels and/or conjugated labeling moieties. The methods of label-free detection can detect small particles such as particles of about 50 nm to about 3000 nm in diameter as a result of the significant signal enhancement achieved by the apparatus described herein. Furthermore, the SERS enhancement is quickly reproducible with a short acquisition time (e.g., 50-100 ms), in part as a result of lacking a memory effect.

Accordingly, the invention provides an apparatus and methods for obtaining a Raman spectrum of a particle, a series of particles, or a compound (an 'analyte'), or for identifying an analyte, as described above. The analyte can be interrogated by a light beam and the scattered light can be gathered and analyzed by a suitable detector (e.g., one capable of detecting light that is Raman scattered from the analyte) to provide valuable information on the analyte. The surface-enhanced Raman spectrum can then be analyzed to identify the analyte from information about its molecular structure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 13A-B. Electropherogram of the three analyte mixture resulting from the CZE separation and detection by LIF. The attenuated signal presented here was extracted from the third avalanche photodiode (APD) on a high dynamic range system equipped with a total of five APDs in series. The signal was treated to account for photon counter dead time (50 ns), background corrected, and a three-point median filter was applied to remove spikes resulting from particulates passing through the detection volume. The experimental conditions (injection time, analyte concentrations, and CZE separation) were kept identical to those used for the CZE-SERS experiments to provide a direct comparison. The LIF electropherogram shows (A) the full scale of the 5-TAMRA peak and (B) all three peaks associated with the elution of R6G (t=187±17 s), RB (t=229±26 s), and 5-TAMRA (t=296±23 s), respectively. The separation efficiencies were calculated from the first APD (no attenuation) using the peak width at baseline and were determined to be 2630±400 theoretical plates for R6G, 6200±600 theoretical plates for RB, and 900±25 theoretical plates for 5-TAMRA. The poor column efficiencies are attributed to the large injection volume and the high concentration of analytes.

FIG. 14A-B. (A) Heatmap of the observed SERS intensity of each Raman shift as a function of migration time for the electophoretic separation of a 102 nL (6 s injection) sample mixture containing $10^{-7}$M R6G, $10^{-8}$ M RB, and $10^{-6}$M 5-TAMRA. (B) SERS intensity profile of the Raman band at 1357 cm$^{-1}$ as a function of migration time extracted from the red rectangle shown in (A). This band is attributed to the combined aromatic C—C and C=N stretching modes in rhodamine compounds. The dashed vertical rectangles in (A) highlight the detection of each analyte.

FIG. 15A-F. Single 50 ms SERS spectrum of (a) R6G ($10^{-7}$ M) extracted from FIG. 14A at t=135 s, (b) RB ($10^{-8}$ M) extracted from FIG. 14A at t=165 s, and (c) 5-TAMRA ($10^{-6}$ M) extracted from FIG. 14A at t=225 s. Averaged SERS spectrum of (d) R6G ($10^{-7}$ M) extracted from FIG. 14A between t=133 and 145 s, (e) RB ($10^{-8}$ M) extracted from FIG. 14A between t=160 and 168 s, and (f) 5-TAMRA ($10^{-6}$ M) extracted from FIG. 14A between t=220 and 226 s. Asterisks indicate the bands intrinsic to each analyte.

DETAILED DESCRIPTION

Figure 1:
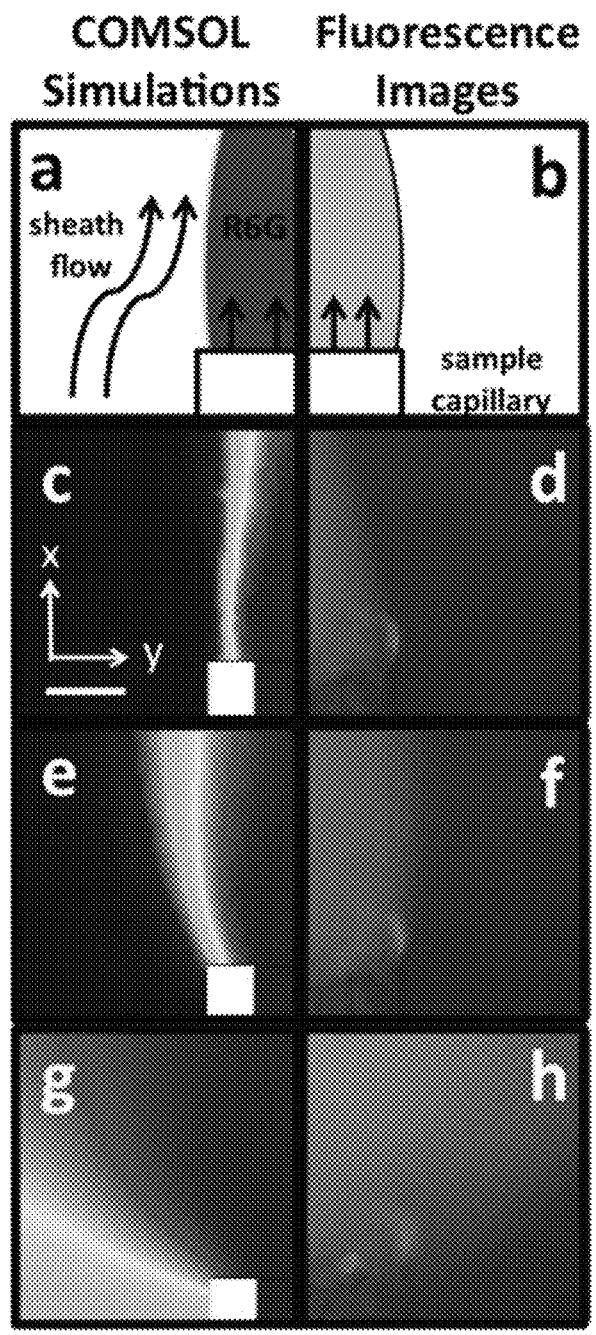
FIG. 1A-H. Schematic representation of a COMSOL simulation (a) and a wide-field fluorescence image (b) showing the analyte eluting from the sample capillary under the influence of the surrounding sheath flow. COMSOL simulations (left panels) showing analyte concentration with corresponding wide-field fluorescence images (right panels) in the xy-plane are depicted at sheath flow rate to capillary flow rate ratios of 36:1 (c) and (d), 10:1 (e) and (f), and ~0 (g) and (h), respectively. The capillary flow rate was held constant. The dimensions and parameter ratios were kept identical for the fluorescence experiments and the COMSOL simulations. The concentration intensity scales from zero concentration (blue) to 1 mM concentration (red) in the COMSOL simulations. Scale bar=75 micrometers.

Label-free, chemical specific detection in flow is important for high throughput characterization of analytes in applications such as flow injection analysis, electrophoresis, and chromatography. We have developed a surface-enhanced Raman scattering (SERS) flow detector capable of ultrasensitive optical detection on the millisecond time scale. The device employs hydrodynamic focusing to improve SERS detection in a flow channel where a sheath flow confines analyte molecules eluted from a fused silica capillary over a planar SERS-active substrate. Increased analyte interactions with the SERS substrate significantly improve detection sensitivity.

The performance of this flow detector was investigated using a combination of finite element simulations, fluorescence imaging, and Raman experiments. Computational fluid dynamics based on finite element analysis was used to optimize the flow conditions. The modeling indicates that a number of factors, such as the capillary dimensions and the ratio of the sheath flow to analyte flow rates, are important for obtaining optimal results. Sample confinement resulting from the flow dynamics was confirmed using wide-field fluorescence imaging of rhodamine 6G (R6G). Raman experiments at different sheath flow rates showed increased sensitivity compared with the modeling predictions, indicating increased adsorption.

Using a 50-millisecond acquisition, a sheath flow rate of 180 µL/min, and a sample flow rate of 5 µL/min, a linear dynamic range from nanomolar to micromolar concentrations of R6G with a LOD of 1 nM is observed. At low analyte concentrations, rapid analyte desorption is observed, enabling repeated and high-throughput SERS detection. The flow detector thus offers substantial advantages over conventional SERS-based assays such as minimal sample volumes and high detection efficiency.

The invention described herein thus provides an apparatus and corresponding methods for the confinement of a sample fluid near a SERS substrate surface to promote interaction between the sample molecules and the SERS substrate. Hydrodynamic focusing is used to confine analytes near the SERS substrate surface. The interaction of two fluid streams at different velocities confine the contents of the slow moving fluid into a volume defined by the flow ratio of the two merging streams. The faster moving stream, or sheath flow, is used to confine the analytes near the SERS substrate surface to provide a detection volume in close proximity to the SERS substrate surface.

Because of the surface sensitivity of SERS, sample confinement with hydrodynamic focusing on a planar surface facilitates SERS detection in flow. A combination of finite element simulations, fluorescence imaging, and Raman experiments were used to investigate the improvement in SERS sensitivity. The results show rapid and efficient detection of analytes, such as rhodamine 6G (R6G), eluted from a capillary and confined onto a SERS-active substrate located at the bottom of the channel using a faster moving sheath flow around the sample capillary outlet.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "an item" includes a plurality of such items, so that reference to item X includes a plurality of items X. It is further noted that the claims may be drafted to exclude any optional item or element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the molecular level, for example, to bring about a chemical reaction or interaction, or a physical change, e.g., in a solution or in a reaction mixture.

Raman spectroscopy refers to a spectroscopic technique used to observe vibrational, rotational, and other low-frequency modes in a system. Raman spectroscopy can be used to provide a fingerprint by which molecules can be identified. Raman spectra inherently contain chemical bonding information in the form of vibrational bands that are unique to particular molecular structures and thus can be used for identification and confirmation purposes. Raman spectroscopy can be used in aqueous solutions and is therefore often the method of choice in bioanalytical and medical studies. Raman detection can be readily interfaced with capillary electrophoresis by adapting an existing setup used in optical detection methods (He et al. (2000) Anal Chem 72:5348-5355).

Surface-enhanced Raman scattering (SERS) is a surface-sensitive technique that enhances Raman scattering by molecules adsorbed on a rough metal surface or adsorbed by nanostructures.

Modeling and Fluorescence Images of Hydrodynamic Focusing on a Surface

Described herein is the use of confinement effects of hydrodynamic focusing to improve measurement sensitivity in microfluidics-based assays to improve SERS detection in flow. Finite element simulations were combined with widefield fluorescence imaging experiments to assess the influence of hydrodynamic focusing on fluid dynamics near the SERS surface.

COMSOL simulations were performed to model the effect of sheath liquid flow dynamics on the sample stream eluting from a capillary placed laterally on a surface. In these calculations, the ratio of the sheath flow rate to that of the sample analyte was varied to assess the analyte confinement onto the surface, where SERS detection occurs. FIG. 1 presents juxtaposed images from the COMSOL simulation in the xy-plane (left) and the corresponding wide-field fluorescence images (right) acquired under equivalent conditions. The first row in FIG. 1 depicts a schematic representation of the analyte eluting from the sample capillary under the influence of the surrounding sheath flow in a COMSOL simulation (FIG. 1a) and a wide-field fluorescence image (FIG. 1b). The experiment was modeled at varying sheath flow rates while the capillary flow was held at a constant rate. Wide-field fluorescence of R6G eluting from the capillary was imaged while varying the sheath flow rate to match the sheath flow rate to capillary flow rate ratios used in the COMSOL simulations. The relative volumetric velocities of the two fluid streams are the important parameter to determine the effect of confinement of the analyte eluted from the capillary by the sheath fluid. The sheath flow to analyte flow rate ratios are 36:1 (FIGS. 1c and 1d), 10:1 (FIGS. 1e and 1f), and ~0 (FIGS. 1g and 1h), respectively.

Using a flow rate ratio of 36:1, the COMSOL simulation predicts a narrow profile for the sample eluting out of the sample capillary (FIG. 1c). The fluorescence image acquired under equivalent conditions (FIG. 1d) shows that the R6G molecules dispensed by the capillary are confined into a cone-like profile by the interaction with the faster moving sheath flow, as predicted. A sheath flow to capillary flow rate ratio of 10:1 results in a broader longitudinal stream of analyte molecules with a width similar to the capillary outer diameter that also matches the model. When the capillary flow rate is greater than sheath fluid velocity, the sample expands and essentially fills the flow chamber. This behavior is clearly observed in both the COMSOL simulation (FIG. 1g) and in the wide field fluorescence images (FIG. 1h).

Figure 2:
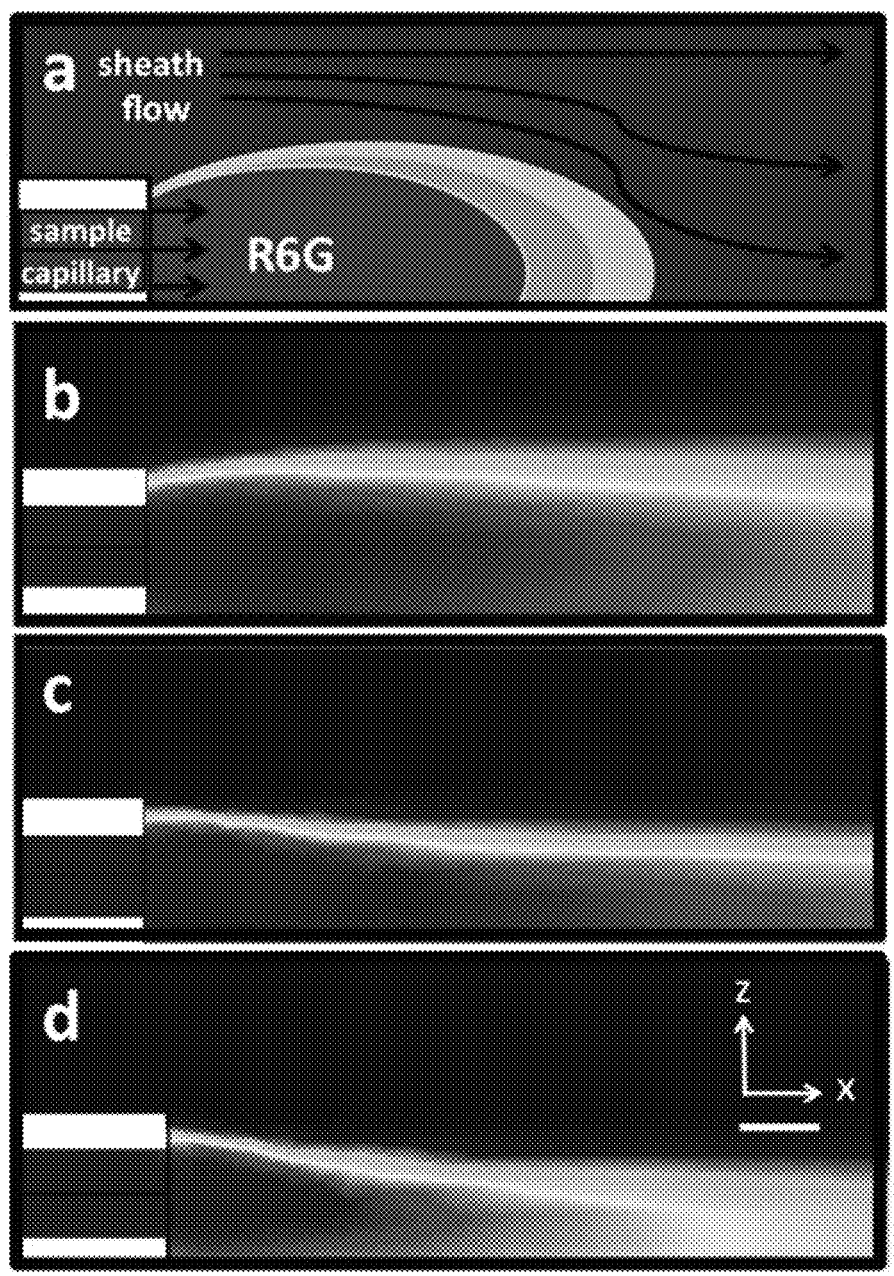
FIG. 2A-D. (a) The flow cell and its components in the xz-plane, normal to the SERS substrate, are shown schematically. COMSOL simulations show the confinement and the predicted analyte concentration at different sheath flow to capillary flow rates. The sheath flow rate to capillary flow rate ratios depicted are: (b) 10:1, (c) 36:1, and (d) 72:1, respectively. The capillary flow rate was held constant. The concentration intensity scales from zero concentration (blue) to 1 mM concentration (red). Scale bar=75 micrometers.

The fluid dynamics simulations provide insight in the confinement of the sample normal to the surface. FIG. 2 shows a schematic representation of the flow cell and its components in the xz-plane, normal to the SERS substrate (FIG. 2a) as well as the simulation results for sheath flow rate to capillary flow rate ratios of 10:1 (FIG. 2b), 36:1 (FIGS. 2c), and 72:1 (FIG. 2d), respectively. The initial increase in the sheath flow shows the expected increase in sample confinement in the z-direction. The sample stream thickness can be calculated from classical hydrodynamics and is related to the ratio of the sheath flow and sample flow rates. With confinement on the surface, the slowed velocity at the walls results in a thicker sample layer. Manz and coworkers accounted for the wall velocity and demonstrated the ratio between the total ($Q_{total}$) and sample ($Q_{sample}$) flow rates scales in relation to the sample layer thickness (d) and the height of the channel (h) as follows:

$$\frac{Q_{sample}}{Q_{Total}} = 3\frac{d^2}{h^2} - 2\frac{d^3}{h^3} \quad (1)$$

Figure 8:
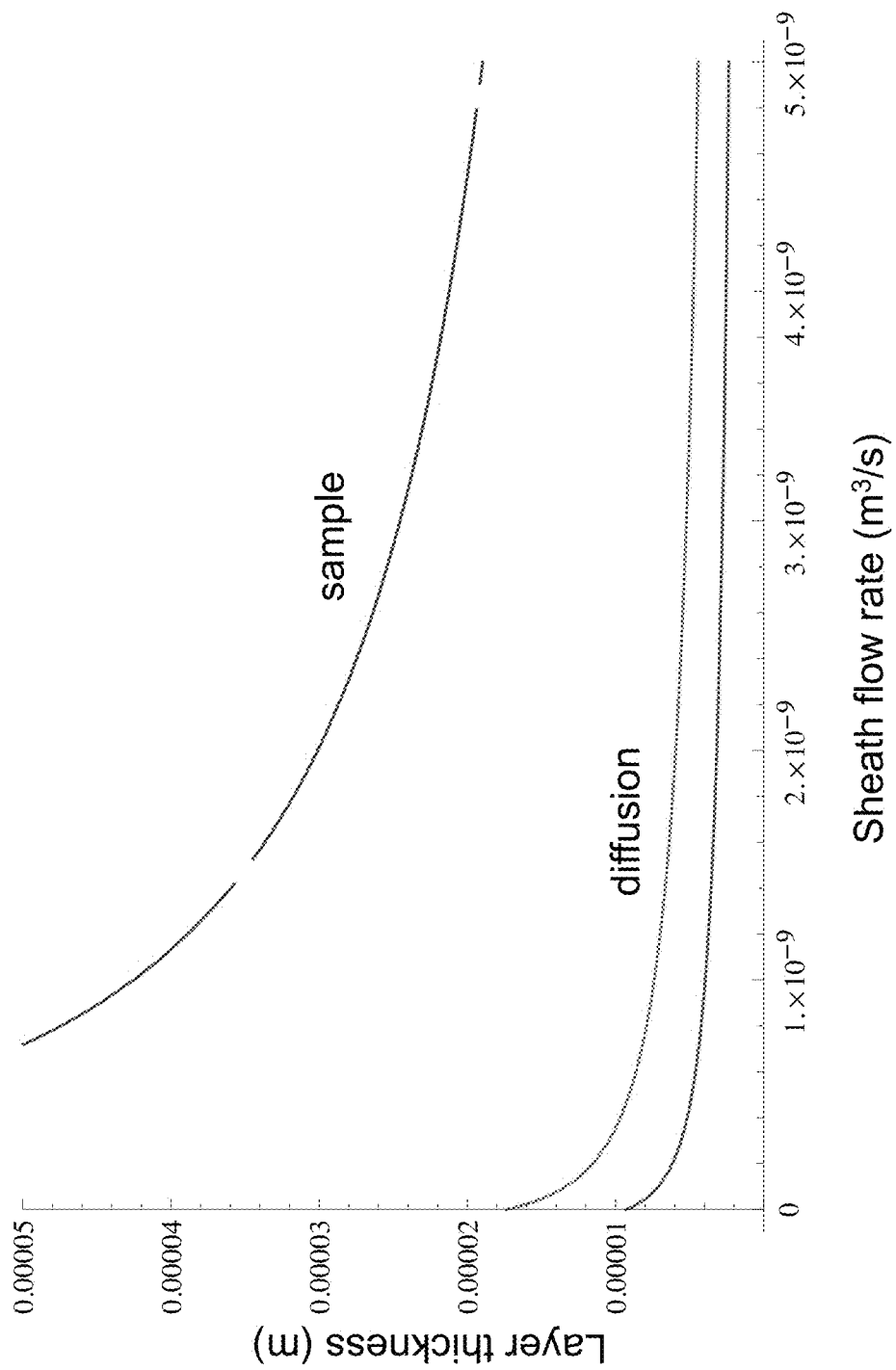
FIG. 8. The sample thickness over the SERS substrate as a function of sheath flow rate was calculated and plotted by solving Equation 1 for the sample thickness using a fixed analyte flow rate of 5 µL/min, a diffusion coefficient of $5 \times 10^{-6}$ $cm^2/s$, and a channel height of 250 µm. The diffusion layer thickness was calculated under these conditions using two methods, one reported by Manz and colleagues (O. Hofmann, G. Voirin, P. Niedermann, A. Manz, *Anal. Chem.* 2002, 74. 5243-5250, DOI: 10.1021/ac025777k) where the diffusion thickness is determined from the mass transport coefficient at a point on the sensor surface, and alternatively integrating across the detection area. Due to the small size of the detection area (laser spot), the difference in the two calculations is small. At the optimal experimental flow rate (180 µL/min=$3 \times 10^{-9}$ $m^3/s$), the calculation shows that additional confinement could further improve SERS detection.

The layer thickness as a function of sheath flow rate can be determined by solving Eq. 1 for d, using a fixed sample flow rate (5 μL/min) and a channel height of 250 μm (see FIG. 8 described in Example 2). Under these conditions, the faster sheath flow confines the molecules into a narrower stream of analyte molecules over the surface.

The simulation of our experimental geometry shows that an optimum sheath flow rate is observed at a ratio of 36:1. FIG. 2d shows the COMSOL simulation at a flow rate ratio of 72:1. At this faster sheath flow rate, there is increased focusing in the xy-plane parallel to the surface; however, the simulation shows decreased analyte concentration on the SERS substrate from what appears to be turbulent flow (FIG. 2d). The sharp edges of the capillary in the flow channel appear to induce turbulence when the sheath flow rate to sample flow rate ratio exceeds 36:1. In the given cell configuration, the onset of turbulence appears to limit the extent of sample confinement associated with hydrodynamic focusing.

The agreement between the fluorescence images and finite-element models show that sample confinement is achieved by hydrodynamic focusing in our SERS flow detector. The COMSOL model indicates the analyte concentration is conserved over finite dimensions as it exits the capillary. From the COMSOL simulation, it is evident that SERS collection should be performed at a distance within 100-200 μm, approximately equal to the sample capillary o.d., which is easily identified in the microscope. In various embodiments, the SERS collection can be performed at a distance within about 50 μm, within about 100 μm, within about 150 μm, within about 200 μm, within about 300 μm, within about 400 μm of the capillary exit, or at a distance approximately equal to 0.5 times to 2 times the sample capillary o.d. from the capillary exit. The combination of COMSOL simulations and wide-field fluorescence imaging experiments indicate that confinement of molecules at the bottom of the flow channel improve SERS detection under controlled conditions.

Improved SERS Detection Using Hydrodynamic Focusing

Figure 3:
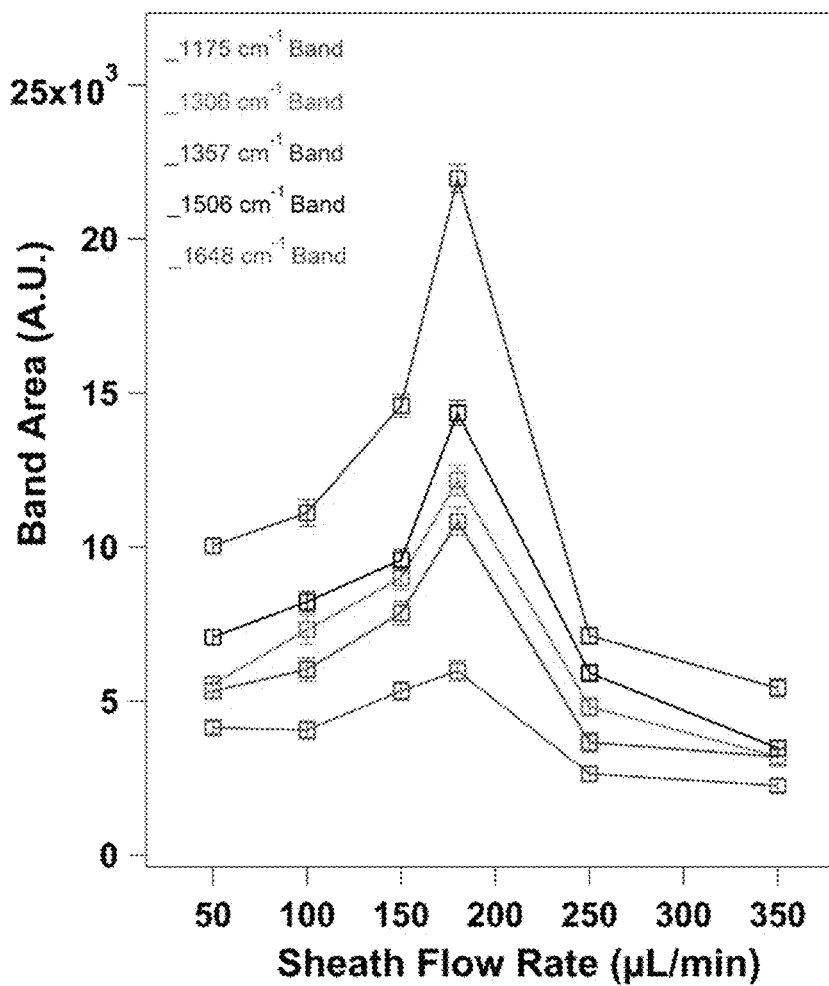
FIG. 3. The areas of the Raman bands at 1174, 1306, 1357, 1506, and 1648 $cm^{-1}$ observed in the SERS spectrum of R6G are plotted as a function of sheath flow rate in the range from 0 to 360 µL/min. The capillary flow rate was held constant at 5 µL/min. Each data point represents the average area of a band taken from 1500 spectra consecutively acquired at 50 ms intervals. Error bars represent the standard deviation.

A series of Raman experiments were performed to assess the sensitivity of the SERS flow detector. R6G was used as the standard model molecule due to its large Raman cross section. To determine the influence of the sheath flow on the SERS signal, the intensity of a $10^{-5}$ M R6G solution eluted from the capillary was measured at different sheath flow rates. FIG. 3 shows a plot of the absolute area of the bands at 1175, 1306, 1357, 1506, and 1648 $cm^{-1}$ in the SERS spectrum of R6G (shown in FIG. 4) as a function of sheath flow rate. The bands in the SERS spectrum of R6G used to quantify the SERS intensity are associated with the characteristic stretching modes of C—H band, C=N, and aromatic C—C stretching bands of R6G, respectively.

The plot shown in FIG. 3 reveals two distinct behaviors. The first portion of the plot demonstrates that increasing the sheath flow rate from 0 to 180 μL/min results in a nonlinear increase in integrated SERS intensity for all five bands in the spectrum of R6G. The sample elutes from the capillary at 5 μL/min, providing a sheath to analyte flow rate ratio of 36:1. This observation is in agreement with the prediction that increasing the sheath flow promotes confinement of analyte molecules eluted from the capillary onto the SERS substrate. As confinement increases, a significant increase in SERS intensity is observed.

As the sheath flow rate is increased further, a marked drop in SERS intensity is noted. The drop in SERS intensity may arise from different effects. First, faster sheath flow decreases the dwell time of the analyte in the SERS-active region, hence limiting signal throughput in the detection volume. Second, the COMSOL simulation suggests turbulent flow at higher sheath flow rates, which may also disturb the concentration of analyte molecules at the SERS-active substrate. Under these conditions, molecules are swept into the sheath fluid before reaching the bottom of the channel where the SERS signal is generated. The results in FIG. 3 agree with the COMSOL simulations and indicate optimal conditions for SERS detection.

The increase in signal associated with the sheath flow detector is different than what is predicted for convective-diffusive, or advective, transport to a surface. Matsuda (*J. Electroanal. Chem.* 1967, 15. 325) solved the advective transport to a surface for a thin layer cell as follows:

$$J = 1.47\left(\frac{DA}{h}\right)^{2/3} CQ^{1/3} \qquad (2)$$

where D is the diffusion coefficient, A is the area of the surface used for detection, h is the height of the channel, C is the sample concentration, and Q is the volumetric flow rate. Increased flow rate should show nonlinear increase reaching a limit, as is observed in our flow cell when the analyte is introduced through the main flow channel (see FIG. 9 described in Example 2). The increase in signal observed in the sheath-flow detector shows behavior that resembles increased interactions at the walls associated with confined geometries. In confined channels, adsorption efficiency increases proportional to the cross-sectional area of the channel. Decreased cross-sectional area improves the efficiency of molecules diffusing to the surface. This behavior indicates that increased transport to the SERS surface plays a role in our detector, which we discuss below.

Flow Cell Sensitivity and Limit of Detection

Our results indicate that hydrodynamic focusing gives rise to the greatest SERS signal at a sheath flow rate of about 180 µL/min. FIG. 4a shows a 50 ms SERS spectrum of a $10^{-5}$ M R6G solution acquired under the optimized conditions. The main features of the R6G spectrum are the bands at 1175, 1306, 1357, 1506, and 1648 $cm^{-1}$ highlighted with the dashed vertical lines. The number and position of the bands in the SERS spectra shown in FIG. 4a are in agreement with those reported from SERS studies of R6G. Using our SERS detector, we have successfully detected R6G in a 1 nM solution. FIG. 4b shows an average of ten 50 ms spectrum of a $10^{-9}$ M R6G solution acquired under the same conditions. The $10^{-9}$ M R6G averaged spectrum shows a relatively high noise, suggesting this concentration is near the limit of detection. However, the Raman bands of R6G can be distinguished from the background spectrum shown in FIG. 4c, demonstrating the high level of sensitivity of the assay at nanomolar concentrations using a short (50 ms) spectral acquisition time.

Figure 4:
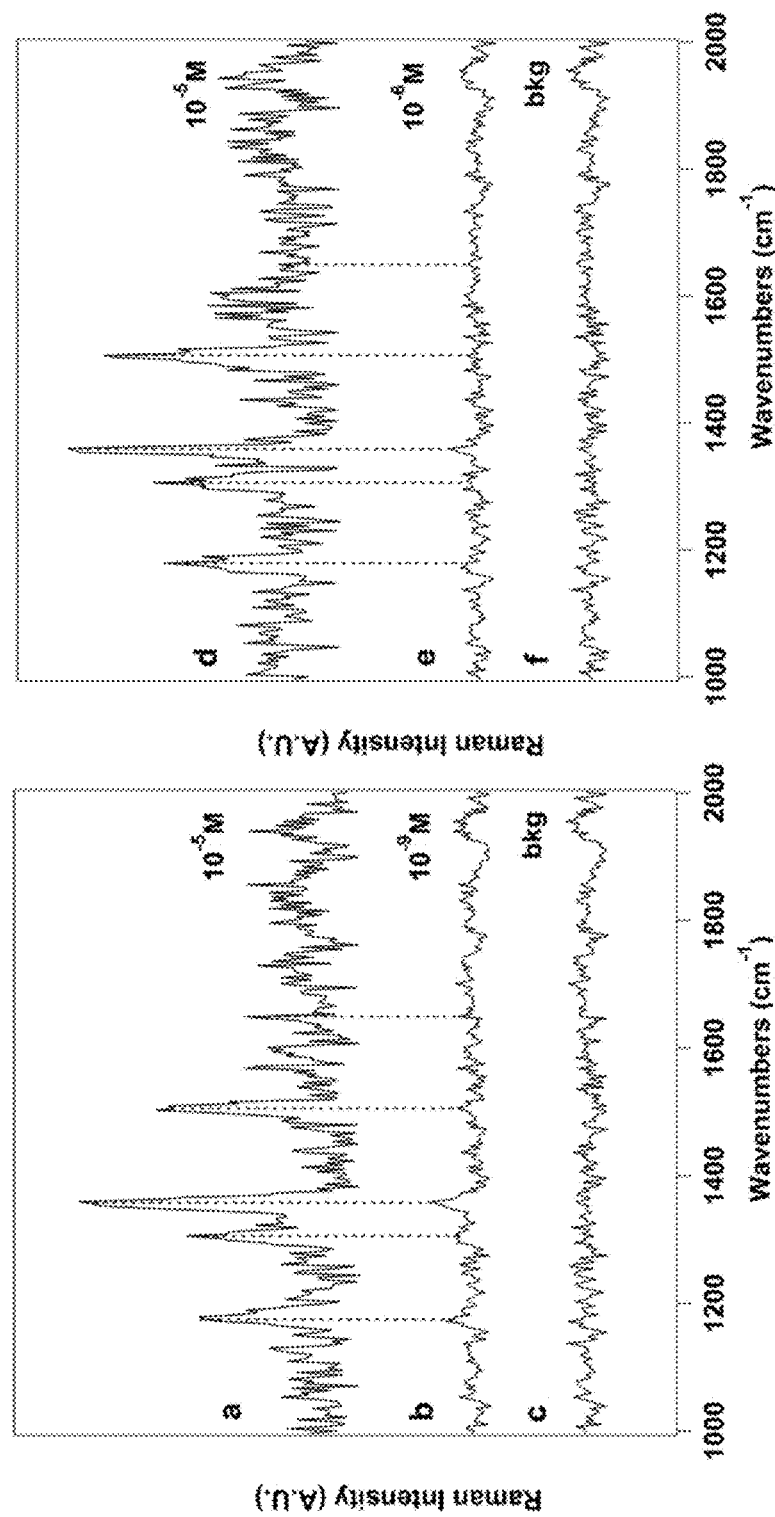
FIG. 4A-F. Spectra obtained with (A) and without (B) hydrodynamic focusing show the increased detection limit achieved with sample confinement. (a) Single SERS spectrum of a $10^{-5}$ M R6G solution, (b) average SERS spectrum of a $10^{-9}$ M R6G solution, and (c) background SERS spectrum collected using a 50 ms spectral acquisition and a sheath flow rate of 180 µL/min. (d) Single SERS spectrum of a $10^{-5}$ M R6G solution, (e) average SERS spectrum of a $10^{-6}$ M R6G solution, and (f) background SERS spectrum collected using a 50 ms spectral acquisition and by flowing the analyte in the flow cell at a flow rate of 150 µL/min. SERS spectra shown in (b) and (e) are averages of 10 individual, 50 ms SERS spectra. The dashed vertical lines in denote the five R6G bands used for analysis.

To assess the improvement in SERS detection using hydrodynamic focusing, the SERS intensity of R6G was measured by injecting the dye analyte into the flow cell without the capillary. For this control experiment, the injection flow rate was optimized to give the highest SERS signal (see FIG. 9 described in Example 2). It was found that in the absence of sheath flow confinement, injecting a $10^{-5}$ M R6G solution at a flow rate of 150 µL/min gave rise to the greatest SERS intensity. FIG. 4d shows a 50 ms SERS spectrum of a $10^{-5}$ M R6G solution acquired under these conditions. The interpretation of this spectrum follows directly from the discussion of the $10^{-5}$ M R6G spectrum shown in FIG. 4a. The two R6G spectra show similar SERS intensity at $10^{-5}$ M. However, the detection limit of the R6G SERS signal is greatly reduced when the sample is introduced directly into the flow cell by syringe pump injection. FIG. 4e shows an average of ten 50 ms spectrum of a $10^{-6}$ M R6G solution. As evident, the R6G SERS signal at this concentration is above the background (FIG. 4f) but near the limit of detection. The results from FIG. 4 demonstrate that the use of hydrodynamic focusing improves the limit of detection by three orders of magnitude compared to simply flowing the analyte over the SERS surface in a larger channel. The limit of detection with hydrodynamic focusing is also three orders of magnitude better than previous reports of R6G with 2-D planar SERS substrates in flow (Leopold and Lendl, *Anal. Bioanal. Chem.* 2010, 396. 2341-2348).

In addition to providing a lower limit of detection, the use of a narrow-bore capillary for sample delivery greatly reduces the required sample volume by four orders of magnitude: ~100 nL instead of ~1 mL when injecting the sample in the flow cell.

Figure 5:
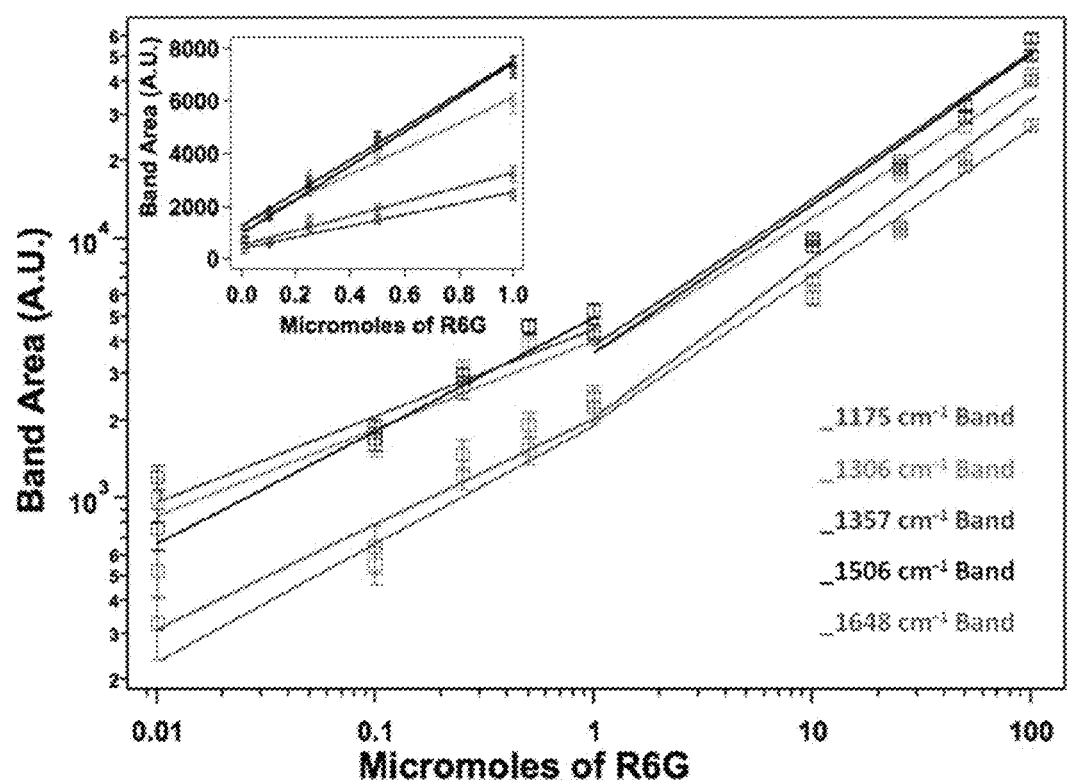
FIG. 5. Log-log plot of the integrated SERS intensity as a function of R6G concentration in the range from $10^{-4}$ to $10^{-9}$ M at each Raman shift frequency. The lines are the fit to an exponential for the two different intensity profile. The inset (plotted in linear scale) shows a linear concentration dependence in integrated SERS intensity for R6G concentrations between $10^{-9}$ and $10^{-6}$ M. Each data point represents the average area of a band taken from 1500 spectra consecutively acquired using a 50 ms acquisition and a sheath flow rate of 180 µL/min. Error bars represent the standard deviation.

The sensitivity of the detector was further investigated by measuring the SERS spectrum of R6G solutions ranging from $1\times10^{-4}$ to $1\times10^{-9}$ M. FIG. 5 shows the log-log plot of the integrated SERS intensity as a function of R6G concentration at each Raman shift frequency. As expected, the plot reveals an increase in band area for all five Raman bands at increasing R6G concentration. Interestingly, the plot does not follow the Langmuir adsorption isotherm typically observed for SERS experiments. Instead, two different sensitivity regimes can be distinguished for each of the 5 bands. The first regime displays a linear increase in integrated SERS intensity of R6G at low concentration ($10^{-9}$ to $10^{-6}$ M). The inset in FIG. 5 (plotted in linear scale) demonstrates the linear dependence of the SERS signal as a function of R6G concentration. The averaged Raman band areas at 1175, 1306, 1357, 1506, and 1648 $cm^{-1}$ over this concentration range have $R^2$ values of 0.9580, 0.9808, 0.9678, 0.9736, and 0.9608, respectively. These regression coefficients support the linearity of the data and demonstrate that the SERS-based flow detector can quantitatively detect R6G in a linear fashion for concentrations ranging from $10^{-6}$ to $10^{-9}$ M.

The second regime appears to show an exponential increase in SERS signal for concentrations greater than $10^{-6}$ M. At these higher concentrations, adsorption to the surface is prominently observed, suggesting more complete monolayer or potentially multilayer effects. Chemical interactions between the R6G molecules and the metallic surface may give rise to additional chemical enhancements that produce the steep increase in signal for concentrations higher than $10^{-6}$ M; however, the relative band intensities and frequencies are unchanged at these higher concentrations arguing against a new complex formation at higher concentrations.

Flow Cell Regeneration

The results presented above suggest that adsorption to the surface plays a role in the increased sensitivity. For high throughput analysis, it is desirable to desorb molecules after detection. One of the advantages of the flow detector is the analyte stream is rapidly depleted of molecules when the sample stream is changed. This attribute of flow detection prevents pooling of analyte molecules. To test the adsorption and desorption properties of the detector, the area of the five Raman bands in the spectrum of R6G was monitored during the course of an experiment where R6G was pumped in, the analyte flow was stopped, and then the cell was flushed with 0.1 M NaOH.

FIG. 6A shows the heatmap of the SERS intensity as a function of Raman shift and time for the injection of $10^{-5}$ M R6G solution, followed by stopping the analyte flow and flushing the sample capillary with NaOH. In FIG. 6A, the temporal behavior of the prominent Raman bands can be divided into five time segments. The first segment corresponds to the first 45 seconds of spectral acquisition and represents the time needed for the $10^{-5}$ M R6G solution in the injection block to travel through the capillary and reach the detection volume in the flow channel (1). The presence of R6G in the detection volume results in an increase in SERS signal followed by an intensity plateau for all five bands from t=45 to 100 sec, as seen in the second segment (2). At t=100 sec, the injection of R6G is stopped, resulting in a rapid decrease in signal for all the bands, as seen in the third segment (3). During this decrease in SERS signal, the analyte in the injection block was changed to a 0.1 M solution of NaOH. At t=150 sec, NaOH was injected into the capillary to flush out the residual R6G present in the capillary, resulting in a second increase in SERS signal from t=150 to 200 sec (4). The last segment (5) corresponds to the elution of NaOH into the detection volume, which results in a rapid decrease in integrated SERS intensity and the return of the signal to baseline level.

FIG. 6B shows the SERS intensity profile at 1357 cm$^{-1}$ (black trace) as a function of acquisition time extracted from FIG. 6A. Analysis of the 1357 cm$^-$ intensity enables quantification of adsorption and desorption rates in the experiment. To determine the on ($\Delta t_m$) and off ($\Delta t_{-m}$) times at which adsorption and desorption of R6G take place, a 9-point Savitzky-Golay filter was applied minimize noise, as indicate by the red trace (FIG. 6B). At equals the time needed for the R6G SERS signal to change between 10% and 90% of its maximum signal intensity. The on times resulting from the increase in R6G signal following the first ($\Delta t_m$) and second ($\Delta t_{m'}$) injection extracted from the red trace were determined to be 8 and 7 seconds, respectively. The on-rate is observed reproducibly as expected. Conversely, the off times resulting from the first decrease in R6G signal ($\Delta t_{-m}$) when the first injection was stopped and the second increase in R6G signal ($\Delta t_{-m'}$) following NaOH injection were determined to be 15 and 6 seconds, respectively. Interestingly, the $\Delta t_{-m'}$ was found to be much less than $\Delta t_{-m}$, suggesting different desorption mechanisms.

Injecting NaOH through the capillary likely displaces the R6G, promoting faster desorption and return of the SERS signal to baseline level. The mechanism of desorption in the absence of NaOH is less clear. There is the possibility that the molecules are photo-degraded, though no evidence of carbonaceous contamination is observed. Any photo-degraded molecules could be swept away by the flow before they can be detected. A second possibility is local heating of the plasmonic surface promotes dissociation.

Figure 6:
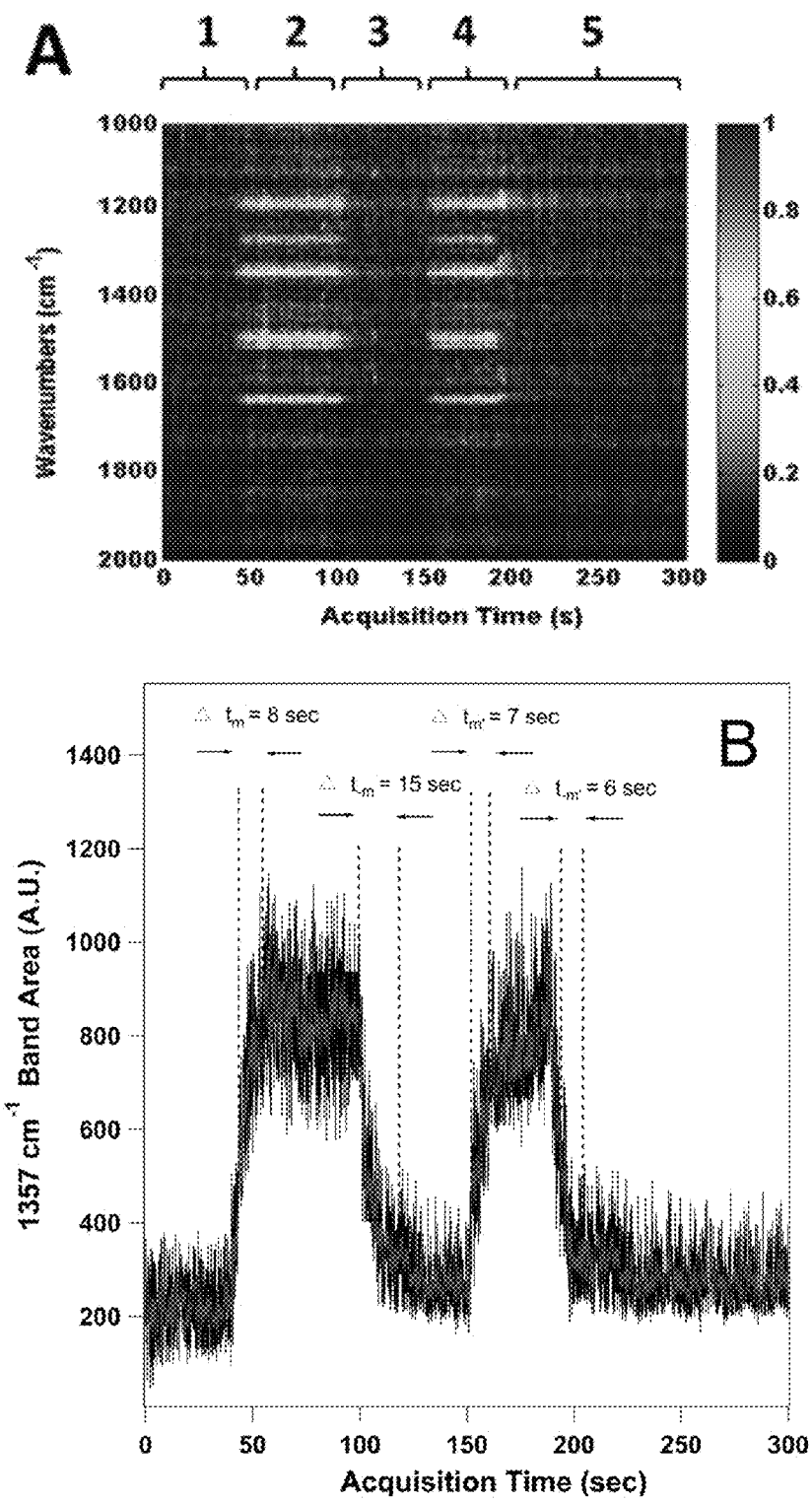
FIG. 6A-B. (A) The heatmap shows the observed SERS intensity at each Raman shift as a function of acquisition time for a $10^{-5}$ M R6G solution during an experiment where the analyte (1) travels through the capillary, (2) is eluted onto the SERS substrate, (3) analyte flow is stopped and a 0.1M NaOH solution is exchanged for the sample, (4) residual analyte in the capillary elutes, and (5) the NaOH solution is eluted. (B) The SERS intensity profile of a single Raman band (1357 $cm^{-1}$) as a function of acquisition time is shown, along with the on ($\Delta t_m$) and off ($\Delta t_{-m}$) times at which adsorption and desorption of R6G take place during the course of the experiment. Of note, the length of segments 1 and 4 are similar, illustrating the time to displace the capillary volume. Spectra were recorded using a 50 ms acquisition and a sheath flow rate of 180 µL/min.

The results from FIG. 6 demonstrate at least two mechanisms for regenerating the SERS surface for subsequent detection. The baseline signals in segments 3 and 5 in FIGS. 6A and 6B show evidence that the R6G molecules are completely desorbed from the silver substrate.

Origin of Increased Sensitivity

The origin of the increased sensitivity at low R6G concentrations appears to arise from improved mass transport and adsorption of analyte to the surface. As noted above, hydrodynamic focusing confines analyte molecules into a region near the sensor surface, resulting in increased interactions with the intense electric field at the surface. The COMSOL model shows the confinement effect; however, the model does not account for analyte absorption, to which we attribute the increased sensitivity. Mass transport to the surface is optimized when the sample layer matches distances associated with diffusion. The nonlinear increase in signal observed with increased confinement (faster sheath flow) supports the idea that increased adsorption efficiency occurs. Adsorption efficiency is aided by constant renewal of the analyte flowing over the surface. As molecules adsorb, the local concentration at the surface increases. Faster adsorption (transport to the surface) results in more molecules in the detection volume and increased signals. In the absence of adsorption, there should be no advantage to sample confinement. Since most molecules adsorb to silver, the increased signals should transfer to other samples in a straightforward manner.

Accordingly, a simple and effective approach for rapid, high throughput SERS detection has been demonstrated using hydrodynamic focusing. The use of sheath flow over a capillary on a surface confines analyte molecules eluted from the capillary over a SERS substrate on the bottom of the flow cell, resulting in greatly improved detection. Simulations and wide-field fluorescence imaging were used in combination to confirm the confinement and determine optimum parameters for SERS detection. Using a 2-D planar substrate, high throughput flow detection of R6G was demonstrated at nanomolar concentrations with acquisition times as short as 50 ms. The current SERS detection strategy provides advantages over the use of colloidal mixtures as sequential on and off detection of R6G was achieved without significant "memory effect" or fouling of the SERS substrate. Additionally, the volume of sample needed for analysis using our flow detector is significantly reduced.

The ultrasensitive on-line SERS detector presented here is straightforward to implement with measurements in flow, such as chromatographic separations. Given the robustness, sample requirement, simplicity, sensitivity, and reproducibility of the current SERS detector, this SERS detection platform has applicability to diverse problems in chemical analysis.

Preparation of Noble Metal Substrate

SERS surfaces can be fabricated with junctions to maximize the enhancements of molecules residing in nanostructure junctions, or 'hotspots', to create highly enhancing surfaces. The signal from a hotspot generates significantly more signal than other, less enhancing sites, and thus it is desirable to maximize the density of hotspots on a surface. The following procedure maximized hotspot density of hotspots. The procedure is described using silver and gold, however, other noble metals may also be used, including platinum, palladium, copper or aluminum.

SERS substrates were prepared by thermal evaporation of either silver (Ag, Sigma-Aldrich, 99.999%) or gold (Au, American Elements, 99.999%) onto a commercial anodized aluminum oxide filter (Anodisc 13, Whatman) with 0.1 μm pores followed by subsequent removal of a porous anodized aluminum oxide (AAO) template. For example, a porous AAO filter is vapor coated with 500 nm of Ag or Au on one side. The metal-coated filter is soaked in thiophenol and then the AAO template is removed by with 0.1 M NaOH. The side of the film nearest to the filter during deposition is a highly effective SERS substrate.

The Anodisc filters were cleaned in Argon plasma for 5 minutes prior to depositing 400-1000 nm of Ag/Au onto a single side of the filter. Deposition was performed at a rate of 1 Å/s. After deposition, the metal-coated filters were stored under vacuum until needed to prevent surface oxidation and contamination. The AAO filter was removed in 0.1 M NaOH (Sigma-Aldrich, 99.99%). After dissolution of the AAO filter, the film was rinsed with ultrapure water (Nanopure, 18.2 MΩ cm). Additional details of the preparation and characterization of the substrate is described by Asiala and Schultz (*Analyst*, 2011, 136, 4472).

For analysis, a self-assembled monolayer of thiophenol was formed on the SERS substrate by soaking in a 10 mM ethanolic solution of thiophenol (Sigma-Aldrich, >99%) for 24 h, rinsing with ethanol, and allowing to dry prior to further experiments. The SERS active metal film is quite thin (≤1 micrometer) and delicate after removal of the AAO template. For experiments, the film can be epoxied to a solid support prior to template dissolution.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Ultrasensitive SERS Flow Detector and Methods of Use

Material and Reagents. Rhodamine 6G (R6G, ~95%) was purchased from Sigma-Aldrich (St. Louis, Mo.). Ultrapure water (18.2 MΩcm) was obtained from a Barnstead Nanopure filtration system. All other chemicals were of analytical grade and used without any further purification.

Substrate Preparation. SERS-active substrates were fabricated by a previously reported thermal evaporation procedure (Asiala and Schultz, *Analyst* 2011, 136. 4472-4479). These substrates were incorporated into a custom-built flow cell by affixing individual substrates onto a standard microscope slide with two 3 mm diameter holes predrilled 35 mm along the center of the slide. Prior to its use, the SERS substrate on the glass slide was soaked overnight in 0.1 M NaOH (Sigma-Aldrich, 99.99%) to dissolve the anodized aluminum oxide (AAO) filter. The resulting SERS-active substrate was thoroughly rinsed with ethanol (Sigma-Aldrich, 99.5%) followed by a final rinse with ultrapure water.

Figure 7:
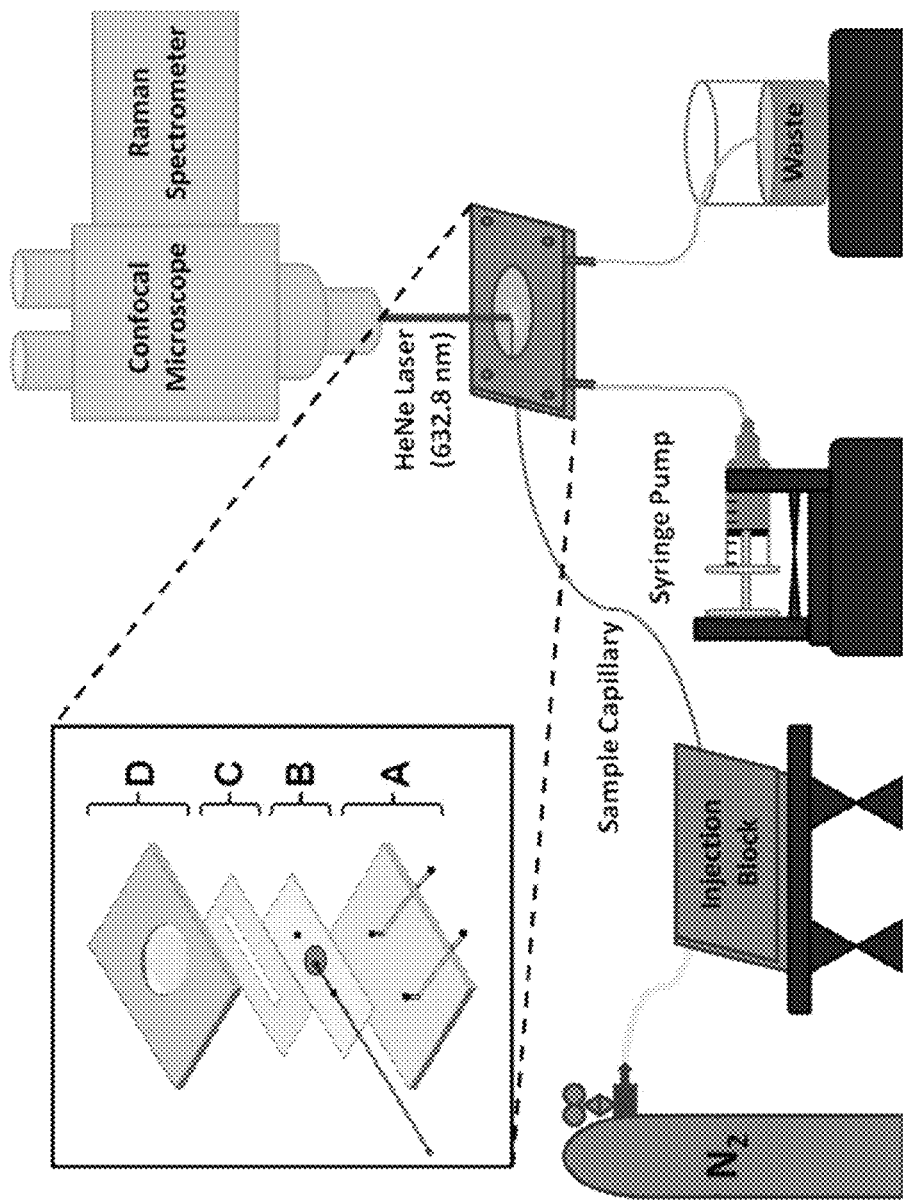
FIG. 7. The schematic diagrams the experimental setup including the Raman microscope, the syringe pump, the waste reservoir, the nitrogen gas tank and the custom-made injection block used to transport the sample through the fused silica capillary to the homebuilt flow cell. The inset shows the different components of the flow cell. The inlet and outlet ports located on the base of the flow cell are used to accommodate the sheath flow (A). Two holes are drilled in a microscope slide defining the sheath flow path and matching the dimensions of the ports. A sample capillary is pinned on a SERS-active substrate mounted in the center of the glass slide (B). Silicone gasket is cut defining the flow channel between the inlet and outlet ports (C). The top of the flow cell is sealed with a glass coverslip held in place by the top plate (D).

Flow Cell Assembly and SERS Detector. FIG. 7 (see Example 2) shows a schematic diagram of the experimental setup. The flow cell included a FEP plastic base plate, a SERS substrate, and a 250 µm thick silicone gasket with a 2 mm slit cut that defined the flow channel, and a stainless steel top plate. The end of a fused silica capillary (Polymicro Technologies, Phoenix Ariz.) with 72 µm i.d., 143 µm o.d., and ~50 cm long was tightly clamped in between the gasket and the substrate to deliver the sample into the detection region. The sample was pressure driven through the capillary at a flow rate of 5 µL/min using a custom-made injection block (Krylov et al., *Anal. Chem.* 2000, 72. 872-877). Hydrodynamic focusing of the sample stream inside the flow chamber was achieved by pumping the sheath liquid (water) continuously through the flow chamber via the inlet port located on the base plate. The sheath liquid flow rate was controlled using a syringe pump (Model NE-500 OEM, New Era Pump Systems Inc., Farmingdale, N.Y.) controlled by LabView software (National Instruments, Austin, Tex.). The liquid was drained out of the flow chamber via the outlet channel connected to the waste reservoir. The flow channel was sealed with a standard cover glass, pressed by the top plate, and secured using 4 tensioning screws.

Raman Measurements. Raman measurements were performed using a previously described system (Asiala and Schultz, *Analyst* 2011, 136. 4472-4479). The sample was illuminated through a 40× water-immersion objective (Olympus, NA=0.8), resulting in a spot size of approximately 0.4 µm². The power of the 632.8 nm HeNe laser was ~1.2 mW, as measured at the sample. Raman back-scattering signal was collected into the same objective lens and directed to the spectrograph and EMCCD (Newton 970, Andor). The flow cell was positioned on the microscope stage and the sheath flow was enabled using the syringe pump. 4000 spectra were recorded in kinetic series with 50 ms acquisition times.

Fluorescence Imaging. Wide-field fluorescence images were acquired using the same microscope described in Example 2 with the following modifications. A 455 nm diode lamp was epi-illuminated onto the sample using a 532 nm laser BrightLine® single-edge laser-flat dichroic beamsplitter (Semrock) and a 10× objective (Olympus, NA=0.5). For this experiment, the capillary was pinned directly to a glass slide in the flow cell. The fluorescent signal was collected through the same objective lens and transmitted back consecutively through the dichroic beamsplitter and a 532 nm RazorEdge® long pass filter (Semrock) before being recorded by an Optixcam summit series 5MP digital camera (Microscope Store, Virginia, USA). Images were recorded at different sheath flow rates using the OC View imaging software.

Data Analysis. Off-line spectral preprocessing and analysis were performed as described in Example 2 below.

COMSOL Simulations. The fluid dynamics inside the flow chamber was modeled using commercial finite element analysis software, Comsol Multiphysics 4.2a, (COMSOL Inc., Burlington, Mass.). A cross-sectional 3-D model was designed in the CAD environment, assuming lateral symmetry as modeled by a mirror plane. The CAD geometry described a cylindrical tube inside a rectangular channel with dimensions matching those of the capillary inside the flow channel. Two equations described the model: Navier-Stokes equations at steady state calculated in the Laminar Flow physics interface, and Fick's law for steady state diffusive transport of solute molecules in the capillary and the flow cell calculated in the Transport of Diluted Species physics interface.

For the flow equation, the boundary conditions include zero velocity at the wall, constant flow rates at the two inlets, pressure with vanishing viscous stress at the flow cell outlet, and continuity boundary condition at the capillary outlet. For the mass transport, the concentration boundary condition is applied to the capillary inlet (1 mM) and flow cell outlet (0 mM). The symmetry and cell walls were modeled with zero normal flux condition. With solute species in relatively low concentrations compared to the solvent (water), it is assumed that a change in solute concentration does not influence the fluid's density and viscosity. This implies that it is possible to solve first for the fluid flow and then for the mass transport. In this model, the solution to the flow equation was used to solve the mass transport equation.

Example 2

SERS Substrate Fabrication, Components, and Experimental Details

This example contains additional experimental details including the SERS substrate fabrication, the technical components used in the Raman microscope, and the data analysis procedures. FIG. 7 depicts the experimental setup as described in the text. FIG. 8 shows the calculated samples thickness as a function of increasing sheath flow rate. FIGS. 9A and 9B show the experimental and calculated effects, respectively, of flow rate on the SERS response observed without hydrodynamic focusing.

Experimental Methods.

Substrate Preparation. Silver (Ag, Sigma-Aldrich, 99.999%) was vapor deposited onto a commercial anodized aluminum oxide filter (Anodisc 13, Whatman) with 0.1 µm pores at a constant rate of 1.0-1.5 Å/s until a quartz crystal microbalance (QCM) registered a final nominal thickness of 500 nm. Prior to deposition, the Anodisc filters were cleaned for 5 minutes in an $Ar^+$ plasma using a plasma cleaner (Model PDC-32G, Harrick Plasma, Ithaca, N.Y.) to remove any surface contamination. Following deposition, the substrates were allowed to cool to room temperature under vacuum inside the deposition chamber for half an hour. The deposited metal films were then removed from the deposition chamber and stored in a vacuum desiccator to prevent oxidation and surface contamination.

Raman Instrument Description. A 17 mW (cw) 632.8 nm HeNe laser (Thorlabs) provided Raman excitation. The laser output was filtered using a 633 nm laser-line filter (Semrocks), half-wave plate (Thorlabs), and thin film polarizer (Thorlabs). The beam diameter was increased using a 5× beam expander (Thorlabs), reflected off a 633 nm notch filter (Edmund Optics) at near normal incidence and coupled to an Olympus microscope through a dual camera port positioned above the BX-51 filter turret where a moveable 90/10 beam splitter (Chroma) directed the laser line to the objective lens. An Andor i303 spectrograph with a 600 groove/mm grating and EMCCD camera (Model Newton 970, Andor) were used in these experiments.

Data Analysis. Off-line spectral preprocessing and analysis were performed using MATLAB software (R2012a, The Mathworks Inc., Natick, Mass.). Baseline correction of the spectra was accomplished in PLS Toolbox version 6.2 (Eigenvector Research Inc., Wenatchee, Wash.) operating in a MATLAB environment, using the preset Weighted Least Squares algorithm function with a $2^{nd}$ order basis filter. Band areas were determined by a Gaussian fit performed with Igor Pro 6.2 (Wavemetrics, Lake Oswego, Oreg.) using a set noise level of 0.0005, a smooth factor of 2, and a minimum fraction of 0.05 for all the spectra acquired.

FIG. 7 is a schematic diagram of the experimental setup including the Raman microscope, the syringe pump, the waste reservoir, the nitrogen gas tank and the custom-made injection block used to transport the sample through the fused silica capillary to the flow cell. The inset shows the different components of the flow cell. The inlet and outlet ports located on the base of the flow cell are used to accommodate the sheath flow (A). Two holes are drilled in a microscope slide defining the sheath flow path and matching the dimensions of the ports. A sample capillary is pinned on a SERS-active substrate mounted in the center of the glass slide (B). A silicone gasket is cut defining the flow channel between the inlet and outlet ports (C). The top of the flow cell is sealed with a glass coverslip held in place by the top plate (D).

FIG. 8 shows the sample thickness over the SERS substrate as a function of sheath flow rate was calculated and plotted by solving Equation 1 for the sample thickness using a fixed analyte flow rate of 5 µL/min, a diffusion coefficient of $5 \times 10^{-6}$ $cm^2/s$, and a channel height of 250 µm. The diffusion layer thickness was calculated under these conditions using two methods, one reported by Manz and colleagues (O. Hofmann, G. Voirin, P. Niedermann, A. Manz, Anal. Chem. 2002, 74. 5243-5250, DOI: 10.1021/ac025777k) where the diffusion thickness is determined from the mass transport coefficient at a point on the sensor surface, and alternatively integrating across the detection area. Due to the small size of the detection area (laser spot), the difference in the two calculations is small. At an optimal experimental flow rate (180 µL/min=$3 \times 10^{-9}$ $m^3$/s), the calculation shows that additional confinement could further improve SERS detection.

Figure 9:
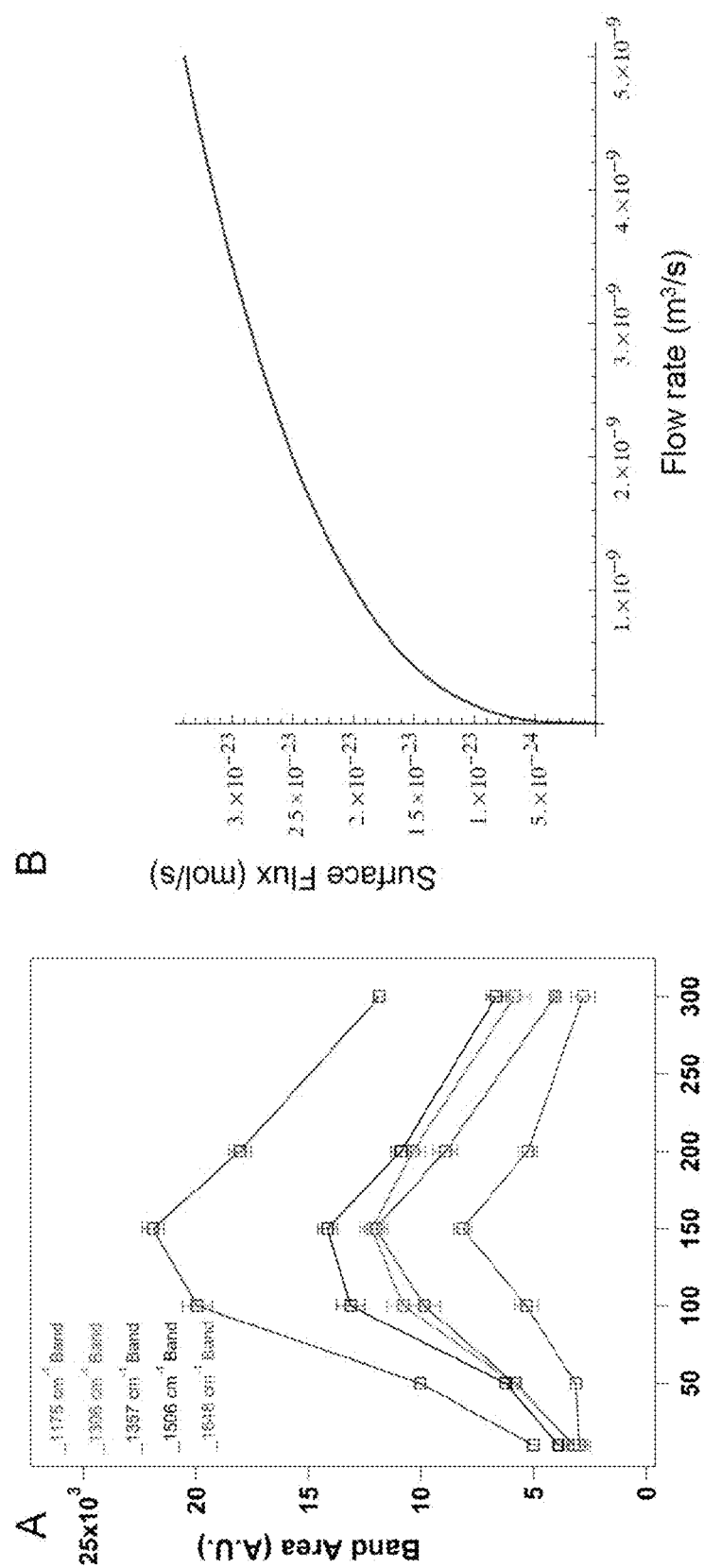
FIG. 9A-B. The experimental (A) and calculated (B) signal dependence associated with increased flux to the surface is shown for experiments performed without hydrodynamic focusing. The experimental result shows an increase in signal with faster flow rates for the prominent rhodamine bands observed in the SERS spectrum. The calculated trend assumes flux to the surface using the analytical solution solved by Matsuda (Equation 2) ((a) S. Sjolander, C. Urbaniczky, *Anal. Chem.* 1991, 63. 2338-2345; (b) H. Matsuda, *Journal of Electroanalytical Chemistry* 1967, 15. 325, DOI: Doi 10.1016/0022-0728(67) 85042-3). At fast flow rates, a decrease in signal suggests the onset of turbulent flow.

FIG. 9 shows the experimental (A) and calculated (B) signal dependence associated with increased flux to the surface is shown for experiments performed without hydrodynamic focusing. The experimental result shows an increase in signal with faster flow rates for the prominent rhodamine bands observed in the SERS spectrum. The calculated trend assumes flux to the surface using the analytical solution solved by Matsuda (Equation 2) ((a) S. Sjolander, C. Urbaniczky, Anal. Chem. 1991, 63. 2338-2345; (b) H. Matsuda, Journal of Electroanalytical Chemistry 1967, 15. 325-&, DOI: Doi 10.1016/0022-0728(67) 85042-3). At fast flow rates, a decrease in signal indicates the onset of turbulent flow.

Example 3

Ultrasensitive Online SERS Detection of Structural Isomers Separated by Capillary Zone Electrophoresis A mixture of structural isomers was separated and identified at nanomolar concentrations (~100,000 molecules) by incorporating capillary zone electrophoresis (CZE) with a sheath flow surface-enhanced Raman scattering (SERS) detector. Baseline resolution was obtained from three structural isomers of rhodamine using a planar silver SERS substrate, demonstrating the utility of this approach for trace chemical analysis.

The ability to identify and characterize molecules purified through separation lies at the heart of chemical analysis. For column-based separations, common methods of detection include UV-visible absorption, laser-induced fluorescence (LIF), and mass spectrometry. Despite its low cost and flexibility, on-column UV-visible absorption suffers from poor molecular specificity and a lack of sensitivity. On the other hand, LIF offers a high degree of sensitivity but requires fluorescent labels. Because structure determination by migration times alone requires extensive knowledge of the samples beforehand, the use of these two methods is limited for explicit analyte characterization. Mass spectrometry provides exquisite analyte identification for many samples. However, many classes of molecules, such as structural isomers and other molecules with the same mass (isobars) are still challenging to characterize. The cost of high-resolution mass spectrometers necessary for characterizing similar compounds limits the utility of this technique for routine characterization. As a result, there is a need for new detection techniques capable of providing structural information with high sensitivity and selectivity for chemical analysis.

In this example we demonstrate surface-enhanced Raman scattering (SERS) for characterization of three rhodamine isomers separated by capillary zone electrophoresis (CZE). CZE is a powerful analytical technique for separation of charged analytes and has been incorporated into microfluidic devices for high efficiency separations. SERS provides extensive structural and quantitative information about a variety of molecules based on their vibrational transitions and can be readily performed in solution to facilitate detection in-line with chemical separations. Given these attributes, SERS can be used to provide chemical identity of solutes following CZE separation, as described herein.

There have been previous attempts to couple SERS to CZE. In these studies, CZE-SERS was accomplished by interfacing detection directly on-column or at-line. Direct on-column SERS detection has been achieved using running buffers containing silver colloidal solutions and by laser-induced growth of silver particles at the end of the capillary. The use of colloidal particles has shown detection limits in the nM or pM range; however, memory effects commonly prevent the regeneration of the detection window and limit these configurations to one-time-use only. Planar SERS substrates in CZE suffer an additional challenge; specifically, a metal in an electric field will form a bipolar electrode and cause electrochemical formation of bubbles and degradation of the sample. In-line CZE-SERS with planar substrates has been limited to μM limits of detection. An at-line approach to CZE-SERS deposits the effluent onto a moving substrate. Drying the sample adsorbs molecules to the surface and avoids challenges associated with mass transport. This approach also avoids challenges associated with the formation of a bipolar electrode across the SERS substrate; however, designing an interface that guarantees maintenance of the electrical current during the deposition onto the substrate is not trivial.

By incorporating our sheath flow SERS detector described herein, we are able to circumvent the challenges noted above and achieve online detection in CZE separations. In particular, the potential drop (bipolar electrode formation) across the SERS substrate is minimized by the increased volume of the sheath flow and confined sample near the electrical ground. Changes observed in the silver oxide background signals suggest a small electrochemical potential is still present. However, we have successfully used the same SERS substrate in CE applications for up to three days without significant signal degradation. The sheath flow SERS detector enables sequential and high throughput detection of the separated dyes at nanomolar concentrations (attomole-femtomole injections) using a 50 ms acquisition without significant "memory effect" or fouling of the SERS substrate.

The sheath flow SERS detector was coupled online to a CZE system. The CZE system is similar to a previously reported system except for the detection module (see Dada et al., *Analyst*, 2012, 137, 3099-3101). CZE separation was performed in positive mode on a 50 cm bare fused silica capillary (Polymicro Technologies, Phoenix, Ariz.) with 72 μm i.d. and 143 μm o.d.

A constant potential of 300 V/cm was supplied by a Spellman, CZE 1000R power supply (Spellman High Voltage Electronics Corp., Hauppauge, N.Y.). The sample, containing $10^{-8}$M rhodamine 6G (R6G), $10^{-10}$ M rhodamine B (RB), and $10^{-7}$ M 5-carboxytetramethylrhodamine (5-TAMRA), was prepared in 15 mM sodium tetraborate buffer (pH 9.4). The CZE separation was performed using a 2 s pressure injection, which injects 34 nL of sample.

Figure 12:
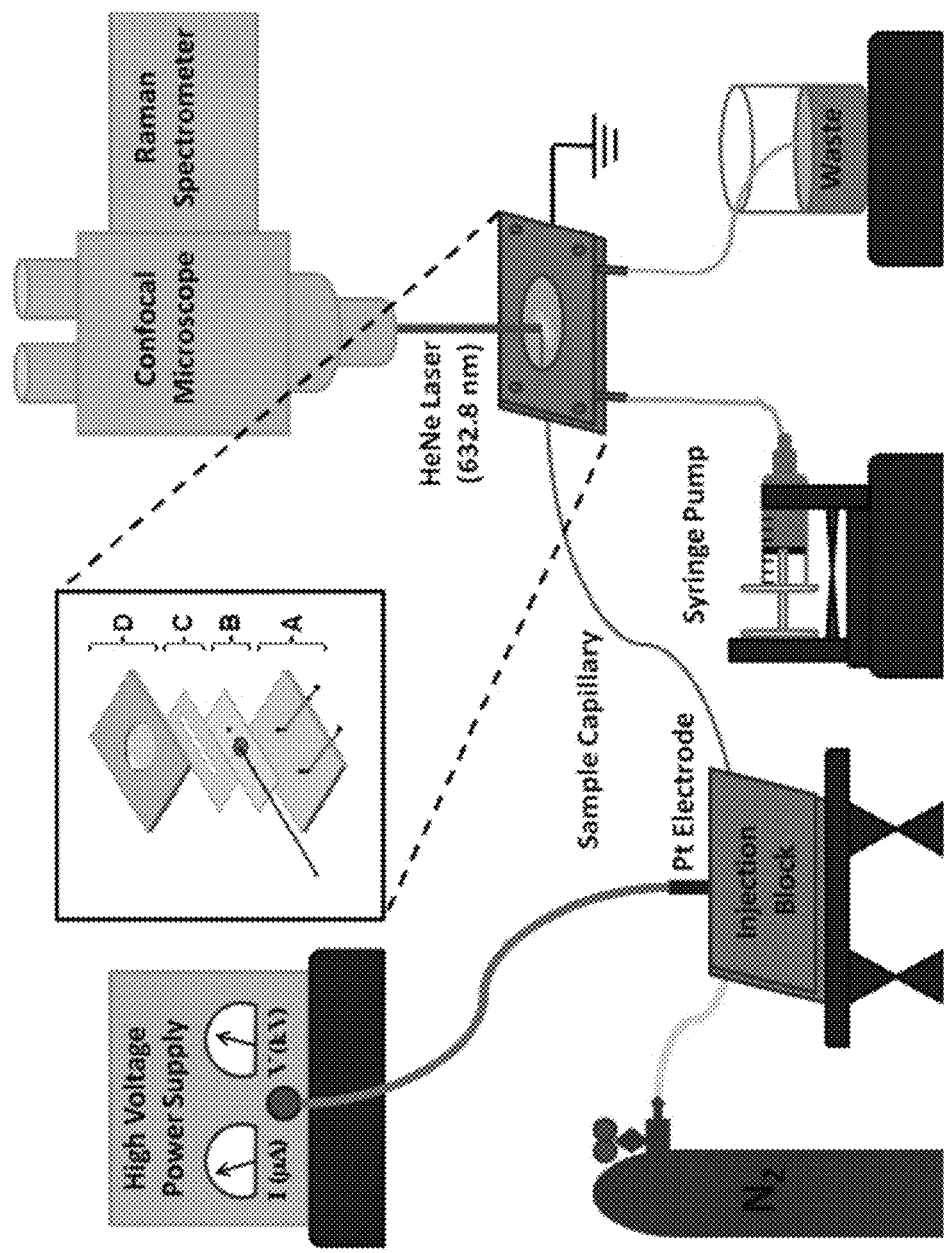
FIG. 12. The schematic diagrams the experimental CZE-SERS setup including the Raman microscope, the syringe pump, the waste reservoir, the nitrogen gas tank, the high voltage power supply, and the Pt electrode embedded in the injection block used to transport the sample through the fused silica capillary to the sheath-flow SERS detector. The inset shows the different components of the flow cell. The inlet and outlet ports located on the base of the flow cell are used to accommodate the sheath flow (A). Two holes are drilled in a microscope slide defining the sheath flow path and matching the dimensions of the ports. A sample capillary is pinned on a SERS-active substrate mounted in the center of the glass slide (B). A silicone gasket is cut defining the flow channel between the inlet and outlet ports (C). The top of the flow cell is sealed with a glass coverslip held in place by the top plate (D).

After injection, the capillary was placed in 15 mM sodium tetraborate buffer solution (pH 9.4) and 15 kV (~40 μA) was applied to the Pt electrode at the sample end of the capillary. SERS measurements were performed in kinetic series with 50 ms acquisition times and by using a sheath flow rate of 10 μL/min (a sheath flow to capillary flow rate ratio of 100:1). The Raman spectrometer used in this study has been previously described (Asiala and Schultz, *Analyst*, 2011, 136, 4472-4479). Raman scattering was detected from a 633 nm laser, away from the absorption band of the rhodamine dyes and thus without the benefit of resonance enhancement. Full details on the instrument setups and experimental procedures are provided in the Experimental Methods section below. FIG. 12 presents the schematic of the experimental setup used for the CZE-SERS experiments.

Figure 10:
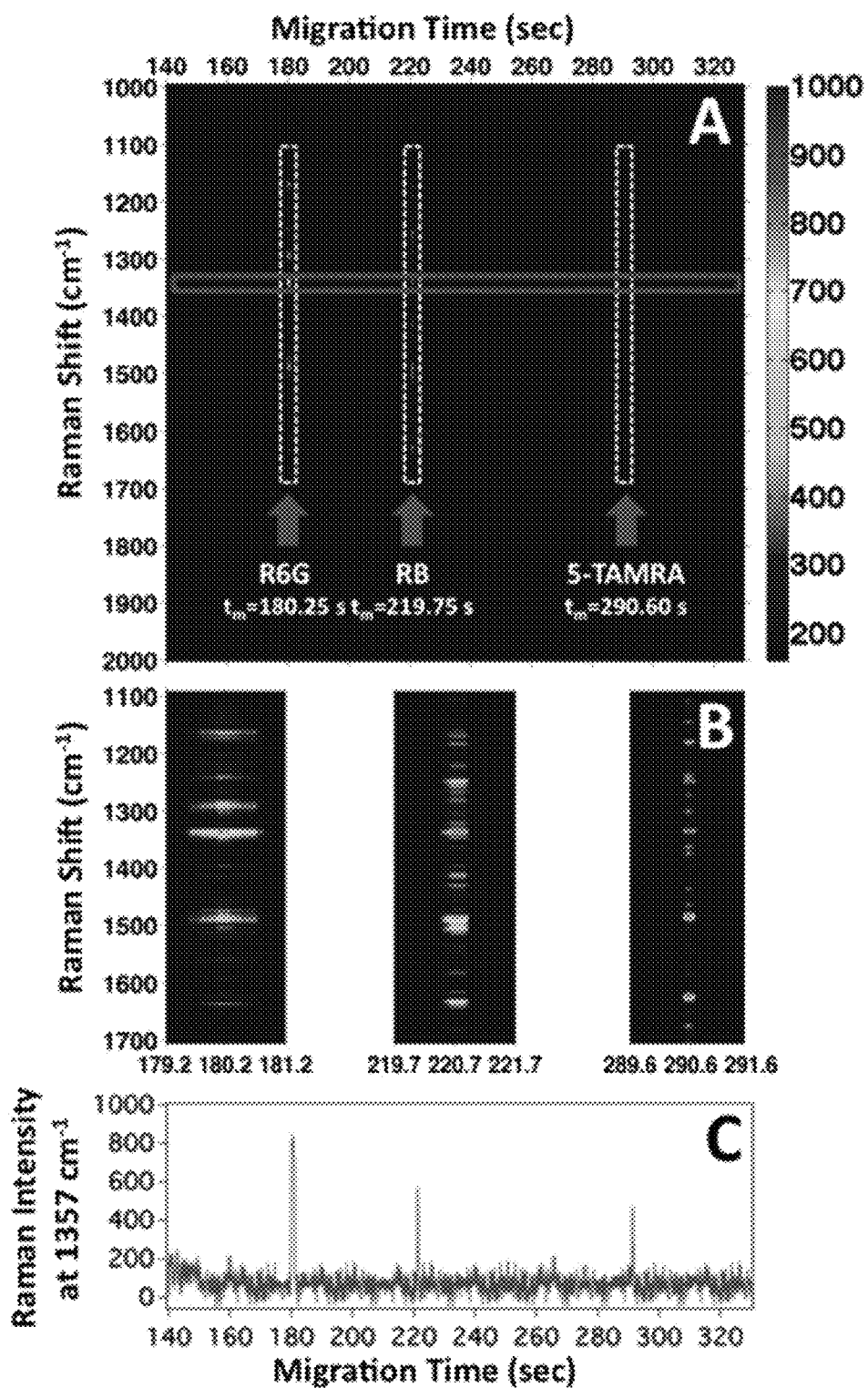
FIG. 10A-C. (A) Heatmap of the observed SERS intensity at each Raman shift as a function of migration time for the electrophoretic separation of R6G, RB, and 5-TAMRA. (B) Zoom in on the dashed vertical rectangles in (A) show 2 s windows corresponding to the detected analytes. (C) SERS intensity profile of the Raman band at 1357 cm-1 is plotted against migration time, extracted from the red rectangle shown in (A). This band is attributed to the combined aromatic C—C and C=N stretching modes of rhodamine compounds. The dashed vertical rectangles in (A) highlight the detection of each analyte.

FIG. 10A shows the heatmap of the SERS intensity as a function of Raman shift and migration time following the electrophoretic separation of three rhodamine isomers (R6G, RB, and 5-TAMRA). The Raman spectrum observed indicates that R6G migrates at $t_m$=180±13 s, RB at $t_m$=220±19 s, and finally 5-TAMRA at $t_m$=290±15 s. The SERS signal for each peak persists for about 1-2 s or less at these low concentrations. The short duration of the SERS signal is more clearly observed in the 2 s zooms shown in FIG. 10B, which illustrate the difference in width of each migration peak.

FIG. 10C shows the SERS electropherogram constructed from the SERS intensity at 1357 cm$^{-1}$ as a function of migration time. This band is attributed to the combined aromatic C—C and C=N stretching modes of rhodamine compounds. The intensity profile at 1357 cm$^{-1}$ provides a convenient signal to characterize the separation efficiency with SERS detection. The spectrally resolved SERS electropherogram of the three rhodamine dyes is characterized by a low and constant background.

Analysis of the SERS electropherogram (FIG. 10C) shows a peak for R6G at t=180.25 s with a full width at half max (FWHM) of 1.25 s, which indicates a separation efficiency of N=115,000±35,000 theoretical plates. The SERS electropherogram peak for RB at t=219.75 s shows a more symmetric peak with a FWHM of 0.55 s. This corresponds to N=898,000±115,000 theoretical plates. The electropherogram peak for 5-TAMRA at t=290.60 s has a FWHM of 0.40 s, which corresponds to a separation efficiency of N=2,900,000±620,000 theoretical plates. Because our analytes fluoresce when excited at shorter wavelengths, we performed laser-induced fluorescence (LIF) to compare the migration times and separation efficiency.

FIG. 13A-B shows the electropherogram of the same three analyte mixture using LIF detection. The analyte concentrations and separation conditions were kept identical to those used in the optimized SERS experiments to provide a direct comparison. The LIF electropherogram shows three bands associated with the elution of R6G, RB, and 5-TAMRA with a separation efficiency N=1,000-6,000 theoretical plates (analyte dependent), which is low for a CZE separation with LIF detection. The poor separation efficiencies are the result of the large injection volume and the high concentration of analytes used for the CZE-LIF experiments. However, CZE-SERS and CZE-LIF generated identical elution order and equivalent migration times under identical separation conditions.

The difference in observed number of theoretical plates provides insight into the mechanism of SERS detection. Only molecules located within a close proximity to the SERS substrate surface can be detected. Our previous work suggests the observed signal arises from adsorbed molecules. However, it is known that Langmuir behavior inhibits analyte adsorption at low concentrations, typically below 1 nM. We have successfully detected RB at a concentration below this in FIG. 10C. This indicates that hydrodynamic confinement can provide a transiently increased concentration at the surface, such that the SERS detection is only obtained from the highest concentration portion of the migrating analyte band. This is in contrast to LIF, where the greater sensitivity enables detection of the width of the entire eluting sample. In FIGS. 14A-B and 15A-F, we show the SERS results from a longer injection and a higher concentration of analytes. The apparent efficiency with SERS detection decreases to a level comparable to LIF due to molecules remaining on the surface for longer periods.

The role of adsorption is further evident in the width of the R6G peak relative to the widths observed for RB and 5-TAMRA. Increased adsorption of R6G to the surface results in a longer observed peak width in the SERS electropherogram (FIG. 10C), indicating R6G has a stronger binding affinity for silver surfaces than RB and 5-TAMRA. The CZE-SERS efficiency appears to correlate to the sample desorption rate from the substrate. In these results, the longer desorption rate observed for R6G can be directly attributed to the difference in molecular structure of the three rhodamine dyes (Scheme 1).

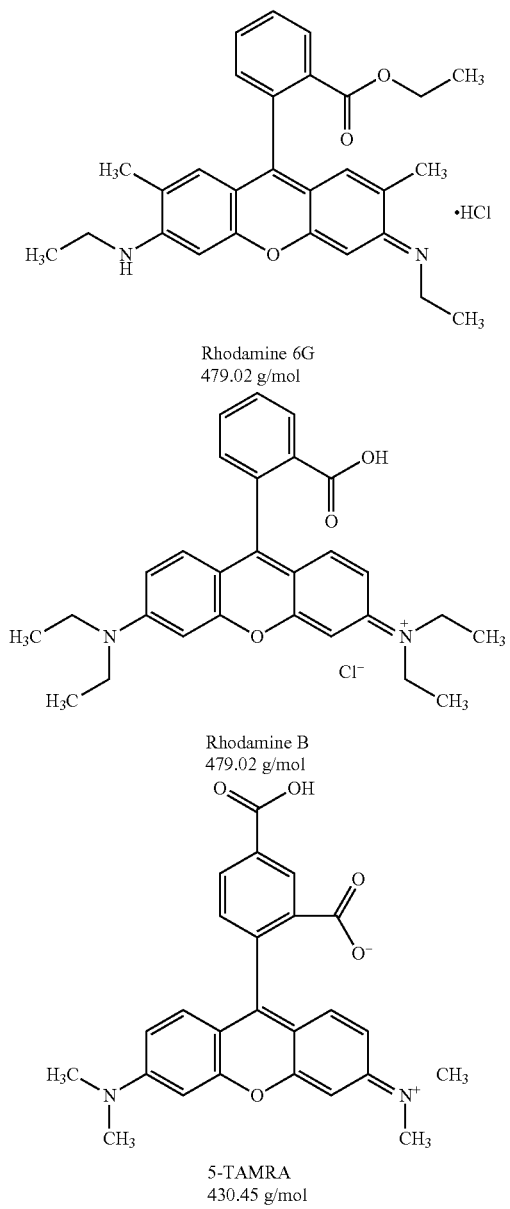

Scheme 1. Molecular structures and molecular weights of the three rhodamine dyes. Of note, rhodamine 6G and rhodamine B have identical molecular weights. Only rhodamine 6G has a secondary amine, to which its strong affinity for the silver SERS substrate can be attributed.

R6G is the only dye out of the three containing a secondary amine group. The pKa of this amine group has a value of 6.13. When dissolved in borate buffer (pH 9.4), the basic form of R6G predominates (pH>pKa). As a result, the secondary amine group is deprotonated and more electron rich. Under these conditions, the nitrogen atom on the R6G molecules is more likely to adsorb to the silver SERS substrate than the other amine groups in RB and 5-TAMRA. These properties explain the higher affinity of R6G for the silver SERS substrate and the resulting slower desorption mechanism observed for this rhodamine dye. Despite these variations, it is worth noting that baseline resolution is achieved between each analyte, demonstrating no memory effects.

In the experiments discussed in Example 1 above, our SERS detector demonstrated a linear response from nM to μM concentrations of R6G, indicating that quantitation is possible for trace analyte detection, and that chemical effects alter the desorption rate.

Figure 11:
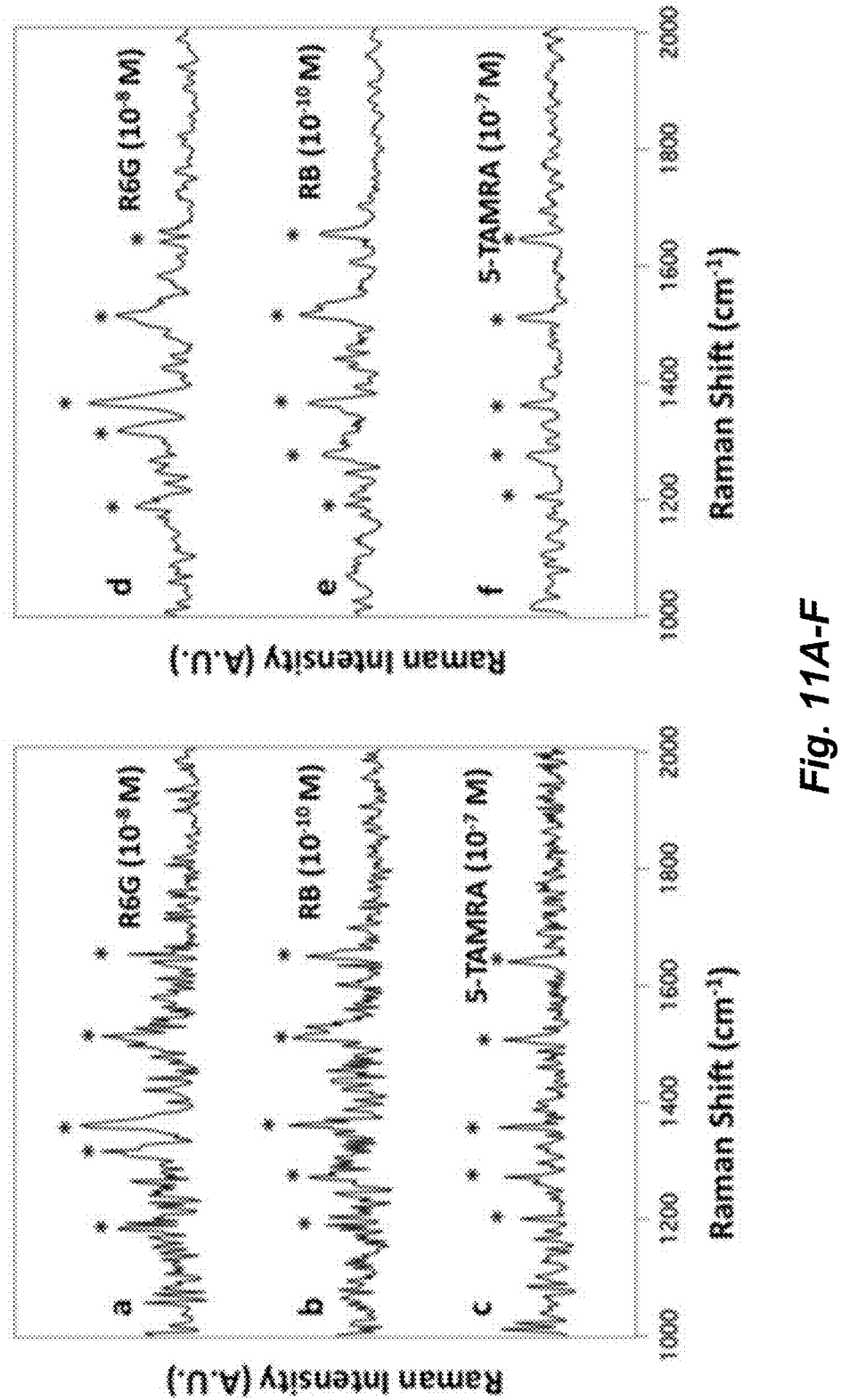
FIG. 11A-F. Single 50 ms SERS spectrum of (a) R6G ($10^{-8}$ M) extracted from FIG. 10A at t=180.25 s, (b) RB ($10^{-10}$ M) extracted at t=219.75 s, and (c) 5-TAMRA ($10^{-7}$ M) extracted at t=290.60 s. The average SERS spectrum of (d) R6G ($10^{-8}$ M) extracted from FIG. 10A between t=179.65 and 180.05 s, (e) RB ($10^{-10}$ M) extracted between t=220.45 and 221.90 s, and (f) 5-TAMRA ($10^{-7}$ M) extracted between t=290.45 and 290.95 s are shown. Asterisks indicate the bands intrinsic to each analyte.

The main advantage of using SERS over conventional detection techniques (UV and LIF) is that it can provide chemical information to identify and characterize analytes beyond migration times. FIG. 11a shows a single 50 ms SERS spectrum of R6G ($10^{-8}$ M) from the electrophoretic separation of the three dye mixture extracted from FIG. 10A at $t_m$=180.25 s. The main features of the R6G spectrum are the bands at 1175, 1306, 1357, 1506, and 1648 cm$^{-1}$. These bands are associated with the characteristic stretching modes of the C—H band, C=N, and aromatic C—C stretching vibrations of R6G. FIG. 11b shows a single 50 ms SERS spectrum of RB ($10^{-10}$ M) extracted from FIG. 10A at $t_m$=219.75 s. The RB bands are assigned to the aromatic C—H bending (1197 cm$^{-1}$), the C—C bridge-bands stretching (1276 cm$^{-1}$), and the aromatic C—H bending vibrations (1357 cm$^{-1}$, 1506 cm$^{-1}$, and 1645 cm$^{-1}$). Finally, FIG. 11c shows a single 50 ms SERS spectrum of 5-TAMRA ($10^{-7}$ M) extracted from FIG. 10A at $t_m$=290.60 s. The main features of the 5-TAMRA spectrum are the bands at 1197, 1276, 1354, 1506, and 1643 cm$^{-1}$. These bands are assigned to the aromatic C—H bending, C—C bridge-band stretching, and aromatic C—C stretching modes of 5-TAMRA.

Averaging the SERS signal over the duration of the electropherogram peak yields spectra with a S/N ratio≥25 for all three analytes. FIG. 11d shows the average SERS spectrum of R6G extracted from FIG. 10A between t=179.65 and 180.05 s. The averaged SERS spectrum of RB extracted between t=220.45 and 220.90 s is shown in FIG. 11e. Of note, the SERS spectrum of RB was acquired from the injection of a few attomoles (~100,000 molecules). FIG. 11f shows the averaged spectrum of 5-TAMRA extracted from FIG. 10A between t=290.45 and 290.80 s. While all three dyes show similar spectra, as expected based on their structures, the differences observed enable identification of the analytes.

Accordingly, we have demonstrated highly sensitive and ultrafast online SERS detection of structural isomers of rhodamine separated by CZE. SERS spectra of the analytes provided direct spectral signatures associated with the subtle structural differences of the three rhodamine dyes. The limit of detection for SERS reported here is more than 1000× better when compared to the best previously reported LOD using a planar substrate (Leopold and Lendl, *Anal Bioanal Chem*, 2010, 396, 2341-2348). The observed Raman scattering allowed differentiation of two isobaric compounds (R6B and RB, M.W=479.02 g/mol) at nanomolar concentrations, which is not achievable by mass spectrometry. The SERS flow detector is readily incorporated into any liquid separation, such as liquid chromatography. The implementation of this robust and sensitive online SERS flow detector provides an alternative for the characterization of pharmaceuticals, metabolites, and other analytes.

Experimental Methods.

Additional experimental details including the SERS substrate fabrication, the technical components used in the Raman microscope, the LIF detector, and descriptions of FIGS. 12, 13A-B, 14A-B, and 15A-F are provided below. FIG. 12 depicts the CZE-SERS experimental setup as described above. FIG. 13A-B presents the electropherogram of the same three analyte mixture described above using LIF detection. FIG. 14A-B shows (A) the heatmap of the SERS intensity as a function of Raman shift and migration time and (B) the SERS electropherogram of the SERS intensity profile of the Raman band at 1357 $cm^{-1}$ as a function of migration time for the CZE separation of the three rhodamine isomers following a 6 s (102 nL) injection of a sample containing $10^{-7}$ M R6G, $10^{-8}$ M RB, and $10^{-6}$ M 5-TAMRA. FIG. 15A-F shows 50 ms (left) and averaged (right) SERS spectra of the three analyte mixture extracted from FIG. 14A.

Material and Reagents. Rhodamine 6G (R6G, ~99%), rhodamine B (RB, ~99%), 5-carboxytetramethylrhodamine (5-TAMRA, ~99%), and sodium tetraborate decahydrate (>99.5) were purchased from Sigma-Aldrich (St. Louis, Mo.). Ultrapure water (18.2 MΩcm) was obtained from a Barnstead Nanopure filtration system. All other chemicals were of analytical grade and used without any further purification.

Substrate Preparation. SERS-active substrates were fabricated by a previously reported thermal evaporation procedure (Asiala and Schultz, *Analyst*, 2011, 136, 4472-4479). These substrates were incorporated into a custom-built flow cell by affixing individual substrates onto a standard microscope slide with two 3 mm diameter holes predrilled 35 mm apart along the center of the slide. Prior to its use, the SERS substrate on the glass slide was soaked overnight in 0.1 M NaOH (Sigma-Aldrich, 99.99%) to dissolve the anodized aluminum oxide (AAO) filter. The resulting SERS-active substrate was thoroughly rinsed with ethanol (Sigma-Aldrich, 99.5%) followed by a final rinse with ultrapure water.

Raman Measurements. Raman measurements were performed using a previously described system (Asiala and Schultz, *Analyst*, 2011, 136, 4472-4479). The sample was illuminated through a 40× water-immersion objective (Olympus, NA=0.8), resulting in a spot size of approximately 0.4 $\mu m^2$. The power of the 632.8 nm HeNe laser was ~1.2 mW, as measured at the sample. Raman back-scattering signal was collected into the same objective lens and directed to the spectrograph and EMCCD (Newton 970, Andor). The spectral resolution of the Raman measurement is about 3 $cm^{-1}$ based on the grating (600 gr/mm), entrance slit (25 µm), monochromator pathlength (320 mm), and CCD pixel size.

CZE-SERS Setup. FIG. 12 shows a schematic diagram of the CZE-SERS experimental setup. The homebuilt flow cell consists of a FEP plastic base plate, a SERS substrate, and a 250 µm thick silicone gasket with a 2 mm slit to define the flow channel, and a stainless steel top plate. The end of a 50 cm bare fused silica capillary (Polymicro Technologies, Phoenix, Ariz.) with 72 µm i.d., 143 µm o.d. was tightly clamped in between the gasket and the substrate to deliver the sample into the detection region. The capillary dimensions were chosen so that the ratio of the o.d. to i.d. is as close to one as possible. Under these conditions, the distance between the molecules eluting from the capillary and the SERS-active substrate is minimized, which increases detection sensitivity. The sample injection was pressure driven through the capillary at a flow rate of 1 µL/min using a custom-made injection block (see Krylov et al., *Anal. Chem.*, 2000, 72, 872-877).

Hydrodynamic focusing of the sample stream inside the flow chamber was achieved by pumping the sheath liquid (15 mM sodium tetraborate buffer, pH 9.4) continuously at a flow rate of 10 µL/min through the flow chamber via the inlet port located on the base plate. The sheath liquid flow rate was controlled using a syringe pump (Model NE-500 OEM, New Era Pump Systems Inc., Farmingdale, N.Y.) controlled by LabView software (National Instruments, Austin, Tex.). The liquid was drained out of the flow chamber via the outlet channel connected to the waste reservoir. The flow channel was sealed with a standard cover glass, pressed by the top plate, and secured using 4 tensioning screws. The system was grounded directly from the SERS substrate during the CZE separations. 6000 spectra were recorded in kinetic series with 50 ms acquisition times.

LIF Measurements: A high dynamic range LIF detector was used in this experiment that has been described elsewhere (Dada et al., *Anal. Chem.*, 2011, 83, 2748-2753). Briefly, fluorescent molecules were excited in a sheath flow cuvette using a 25 mW CW 532 nm diode-pumped laser (CrystalLaser, Model CL532-025) and fluorescence emission was collected through a 600 nm DF 40 bandpass filter at a 90° angle relative to the incident laser beam. Fluorescence was detected using cascaded single-photon counting avalanche photodiode modules (Perkin Elmer, Montreal, PC Canada). The dye concentrations used for the CZE-LIF experiments were identical to those used in the CZE-SERS experiments to provide a direct comparison.

In FIG. 14A, the analytes are assigned based on the observed Raman spectrum, indicating that R6G migrates at t=135±13 s, RB at t=160±15 s, and finally 5-TAMRA at t=220±10 s. Clearly, the spectrally resolved SERS electropherogram of the three rhodamine dyes is characterized by a low and constant background. FIG. 14B shows the SERS electropherogram constructed from the SERS intensity at 1357 $cm^{-1}$ as a function of migration time. The electropherogram peak for R6G shows a broad feature at t=135 s with a full width at half max (FWHM) of 12 s, which corresponds to a separation efficiency N=700±160 theoretical plates. The SERS electropherogram peak for RB at t=160 s shows a more symmetric peak with a FWHM of 6 s. This corresponds to N=3,940±1200 theoretical plates. The electropherogram peak for TAMRA at t=220 s has a FWHM of 4 s and a separation efficiency N=16,760±3600 plates. Similarly poor numbers of theoretical plates was observed with CE-LIF and corresponds the long initial injection time and the high concentration of the sample into the capillary. The strong adsorption of R6G to the SERS substrate is clearly evident by the significant tailing noted in this measurement. This is in contrast with the sharper migration peaks and resulting higher column efficiencies observed for RB and 5-TAMRA, which indicates a faster desorption mechanism.

The SERS response from the substrate is highly reproducible; however, the signal is also a function of the where the laser is focused in relation to where the sheath flow confines the molecules in the detection area. We have found it is important to collect signal from this optimum point in the sheath flow.

Example 4

Online SERS Detection of the 20 Proteinogenic L-Amino Acids Separated by Capillary Zone Electrophoresis A sheath-flow surface-enhanced Raman scattering (SERS) detector was used to provide chemical information enabling identification of the 20 proteinogenic L-amino acids separated by capillary zone electrophoresis (CZE), as described in *Analyst,* 2014, 139, 5989, which is incorporated herein by reference. Amino acids were used to illustrate the chemical specificity of SERS detection from structurally related molecules. Analysis of the SERS electropherograms obtained from the separation and sequential online detection of six groups of structurally related amino acids shows that our sheath-flow SERS detector is able to resolve the characteristic Raman bands attributed to the amine, carboxyl, and side chain constituents. The results demonstrate the chemical information available from our detector and also provide insight into the nature of the analyte interaction with the silver SERS substrate.

The spectra extracted from the SERS electropherogram of a mixture containing the 20 proteinogenic L-amino acids show unique signatures characteristic to each amino acid, thus enabling identification. The results demonstrate the potential of this sheath-flow SERS detector as a general purpose method for high throughput characterization and identification following separations of complex biomolecular mixtures.

We demonstrated sensitive and reproducible online SERS detection of the 20 proteinogenic L-amino acids separated by capillary zone electrophoresis. The sheath-flow SERS detector was sensitive enough to detect amino acids at varying micromolar concentrations. The biochemical variation in the 20 amino acids provided spectral features that can differentiate each amino acid. A mixture of the 20 proteinogenic L-amino acids was separated and identified at micromolar concentrations using 100 ms spectra sequentially collected, demonstrating the ability of the sheath-flow SERS detector to characterize complex mixtures. The spectral reproducibility observed in this study indicates that each amino acid evinces a unique spectrum that can be used for identification, with library matching. The surface selection inherent to SERS provides insight into how the analytes interact with the SERS substrate. The current sheath-flow SERS detector provides complementary characterization to mass spectrometry and improved chemical identification over UV-visible absorption used for post-chromatographic detection. The results demonstrate a fast, robust, reproducible, high throughput, and chemical specific SERS detector for online use with chemical separations.

Example 5

Online SERS Detection of Eight Biologically-Active Peptides Separated by Capillary Zone Electrophoresis We used sheath-flow surface-enhanced Raman scattering (SERS) to analyze a mixture of eight biologically-active peptides separated by capillary zone electrophoresis (CZE), as described in *Analyst,* 2015, 140, 1516, which is incorporated herein by reference. Analysis of the SERS electropherogram resulting from online detection resolves the characteristic Raman bands attributed to the amino acid constituents of each peptide, which enables identification. The detection limit by SERS was found to be $10^{-8}$ M.

Our results indicate that the structural information obtained from the detected vibrational modes provides complementary characterization to other chemically specific detectors like mass spectrometry and improved chemical identification over other commonly used optical-based post-chromatographic detection methods. In addition, the sheath-flow SERS detection results in band narrowing in the observed electropherogram that enables distinction of closely migrating species. The results indicate that this platform can provide fast, robust, reproducible, and chemical specific detection to facilitate the characterization of peptides.

We demonstrated the ability of our sheath-flow SERS detector to characterize and identify eight biologically-active peptides separated by CZE. CZE-ESI-MS was used to confirm the identity, the elution order and the migration times of the peptides observed in the CZE-SERS experiments. The reproducible SERS results provide a chemical specific signature that, once defined, can also be used for identification. More specifically, our sheath-flow SERS detector appears to be sensitive to the characteristic functional groups of aromatic and sulfur containing amino acids, as well as the amine, carboxyl, and side chain constituents located at the N- and C-termini of the peptides. The SERS assay had a limit of detection of $10^{-8}$ M in these experiments. This limit of detection appears to be limited by the Langmuir adsorption behavior. Hierarchical clustering analysis of the SERS spectra can be used to identify differences in the molecular composition of closely-related analytes.

Classic molecular characterization consists of combining orthogonal detection methods. Here we used of our sheath-flow SERS detector with CZE for trace molecule characterization in solution. The implementation of this robust, sensitive and high throughput sheath-flow SERS detector provides complementary characterization to mass spectrometry and improved chemical identification of complex biomolecular mixtures over other commonly used post-chromatographic detection methods for analytes with high biochemical relevance.

Example 6

Sheath-Flow Microfluidic Approach for Combined Surface Enhanced Raman Scattering and Electrochemical Detection The combination of hydrodynamic focusing with embedded capillaries in a microfluidic device enables both surface enhanced Raman scattering (SERS) and electrochemical characterization of analytes at nanomolar concentrations in flow. The approach utilized a versatile polystyrene device that contains an encapsulated microelectrode and fluidic tubing, which is shown to enable straightforward hydrodynamic focusing onto the electrode surface to improve detection. A polydimethyslsiloxane (PDMS) microchannel positioned over both the embedded tubing and SERS active electrode (aligned ~200 µm from each other) generates a sheath flow that confines the analyte molecules eluting from the embedded tubing over the SERS electrode, increasing the interaction between Riboflavin (vitamin B2) and the SERS active electrode. The microfluidic device was characterized using finite element simulations, amperometry, and Raman experiments. This device shows a SERS and amperometric detection limit near 1 and 100 nM, respectively. This combination of SERS and amperometry in a single device provides an improved method to identify and quantify electroactive analytes over either technique independently.

The invention thus provides a unique microfluidic approach using hydrodynamic focusing and combining SERS with amperometry for high throughput detection. The microfluidic device maintains the advantages of sheath-flow SERS detection in a compact design. These advantages include fast detection, high throughput, better signal-to-noise, lower limits of detection, and non-fouling of the analyte to the SERS electrode. This means that appreciable signal can be observed with small sample volumes. The addition of a PDMS microchannel over a polystyrene embedded capillary and microelectrode provides a smaller total volume, a reduced dead volume, and a controlled fluidic environment to confine the analyte eluting from the capillary onto the microelectrode for simultaneous SERS and amperometric detection. SERS detection of riboflavin was demonstrated at a concentration of 1 nM, while the electrochemical detection limit is 89 nM. This device provides a straightforward route to improving trace detection both spectroscopically and electrochemically.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. An apparatus for performing surface-enhanced Raman scattering (SERS) comprising:
   a Raman microscope,
   a flow cell,
   a first pumping apparatus configured for supplying a sheath fluid at flow rate (A) to the flow cell,
   a second pumping apparatus to pump a sample fluid solution,
   a narrow-bore capillary leading from the second pumping apparatus to the flow cell, and
   a detector for detecting light scattered by an analyte dissolved in the sample fluid solution,
   wherein the second pumping apparatus is configured to transport an analyte in solution through the capillary to the flow cell at flow rate (B) that is one-tenth or less than the volumetric velocity of (A), wherein the flow cell comprises:
   an inlet port for the sheath fluid and an outlet port to drain fluids,
   a planar noble metal SERS-active substrate,
   the capillary that connects the second pumping apparatus to the SERS-active substrate of the flow cell, wherein the end of the capillary terminates at an analyte analysis zone accessible to a laser,
   a flow channel extending from the end of the capillary and through the analyte analysis zone for analysis by a laser, and which concurrently defines a flow path between the inlet port and the outlet port, and
   a flow cell cover through which a laser can be directed, which flow cell cover seals the flow cell to prevent fluid from escaping the flow cell except through the outlet port;
   wherein the end of the capillary is directed toward the surface of the SERS-active substrate and the flow cell is configured to perform hydrodynamic focusing on an analyte dissolved in the sample fluid solution, wherein the volumetric velocities of (A) and (B) confine the width of the sample fluid solution exiting the capillary to a longitudinal stream, parallel to the plane of the SERS-active substrate surface at a width about or less than the thickness of the capillary's outer diameter, and confine the analytes in solution normal to the surface of the SERS-active substrate, thereby increasing adsorption of the analytes and providing a detection volume in close proximity to said surface.

2. The apparatus of claim 1 wherein the SERS-active substrate comprises a thin film of silver metal or gold metal.

3. The apparatus of claim 1 wherein the capillary leading to the flow cell is a fused silica capillary.

4. The apparatus of claim 1 wherein the capillary has an outer diameter of about 40 µm to about 300 µm.

5. The apparatus of claim 1 wherein the capillary has an outer diameter of about 50 µm to about 150 µm.

6. The apparatus of claim 1 wherein the capillary has an inner diameter of about 4 µm to about 100 µm.

7. The apparatus of claim 1 wherein the capillary has an inner diameter of about 10 µm to about 50 µm.

8. The apparatus of claim 1 wherein the Raman microscope includes a single longitudinal mode laser with a wavelength between about 632 nm and about 670 nm.

9. The apparatus of claim 1 wherein the sample capillary is connected to a direct output of a chemical separation for repeated analysis.

10. A method of detecting or characterizing an analyte in solution using the surface-enhanced Raman scattering (SERS) flow detector of claim 1, the method comprising:
    contacting an analyte solution and a SERS-active substrate using hydrodynamic focusing to co-locate the analyte on the SERS-active substrate;
    wherein the hydrodynamic focusing comprises passing a sheath fluid over the analyte in solution, wherein the ratio of the sheath flow rate (A) to the capillary flow rate (B) is at least 10(A):1(B), thereby increasing the adsorption of analytes in the detection area of the SERS-active substrate;
    conducting laser excitation of the analyte on the SERS-active substrate; and
    detecting light scattered by the analyte in solution;
    wherein the hydrodynamic focusing on the analyte solution confines the analyte at the SERS substrate, thereby increasing the frequency of interactions between the analyte and nanostructures of the SERS-active substrate, and improves the limit of detection for SERS detection.

11. The method of claim 10 wherein the ratio of the sheath flow rate (A) to the capillary flow rate (B) is about 10(A):1(B) to about 70(A):1(B).

12. The method of claim 10 wherein the ratio of the sheath flow rate (A) to the capillary flow rate (B) is about 12(A):1(B) to about 50(A):1(B).

13. The method of claim 10 wherein the ratio of the sheath flow rate (A) to the capillary flow rate (B) is about 25(A):1(B) to about 45(A):1(B).

14. The method of claim 10 wherein the sheath flow rate is about 50 µL/min to about 360 µL/min.

15. The method of claim 10 wherein the sheath flow rate is about 150 µL/min to about 200 µL/min.

16. The method of claim 10 wherein the range of particle size detection of the flow detector is about 3000 nm to about 50 nm.

17. The method of claim 10 wherein the lower detection limit of the flow detector for solutions is about 100 picomolar.

18. The method of claim 10 wherein the signal of the Raman spectra collected is enhanced by about $10^6$ to about $10^8$ compared to a corresponding spontaneous Raman analysis that does not employ hydrodynamic focusing and SERS.

19. The method of claim 10 wherein the signal of the Raman spectra collected is enhanced by about $10^3$ to $10^4$ compared to a corresponding SERS analysis that does not employ hydrodynamic focusing.

20. The method of claim 10 wherein the SERS-active substrate comprises a thin film of silver metal and the surface of the substrate resists fouling and lacks a memory effect of the analyte.

* * * * *